(12) United States Patent (10) Patent No.: US 9,304,087 B2
Yamada (45) Date of Patent: Apr. 5, 2016

(54) RAMAN SPECTROSCOPIC APPARATUS, RAMAN SPECTROSCOPIC METHOD, AND ELECTRONIC APPARATUS

(71) Applicant: Seiko Epson Corporation, Tokyo (JP)

(72) Inventor: Kohei Yamada, Suwa (JP)

(73) Assignee: Seiko Epson Corporation (JP)

( * ) Notice: Subject to any disclaimer, the term of this patent is extended or adjusted under 35 U.S.C. 154(b) by 21 days.

(21) Appl. No.: 14/477,063

(22) Filed: Sep. 4, 2014

(65) Prior Publication Data

US 2015/0064778 A1 Mar. 5, 2015

(30) Foreign Application Priority Data

Sep. 5, 2013 (JP) ................. 2013-183944

(51) Int. Cl.
  *G01J 3/44* (2006.01)
  *G01N 21/65* (2006.01)
  *G01N 33/00* (2006.01)
  *G01J 3/02* (2006.01)

(52) U.S. Cl.
  CPC .......... *G01N 21/658* (2013.01); *G01N 33/0047* (2013.01); *G01J 3/02* (2013.01); *G01J 3/44* (2013.01)

(58) Field of Classification Search
  CPC ....... G01N 21/62; G01N 21/67; G01N 21/69; G01N 21/3103; G01J 3/443
  USPC .................................. 356/300–445
  See application file for complete search history.

(56) References Cited

U.S. PATENT DOCUMENTS

| 7,351,588 | B2 | 4/2008 | Poponin |
| 7,709,810 | B2 | 5/2010 | Misawa et al. |
| 2007/0134805 | A1 | 6/2007 | Gilbert |
| 2007/0292735 | A1* | 12/2007 | McMahon .............. H01M 4/86 429/431 |

(Continued)

FOREIGN PATENT DOCUMENTS

| JP | 2009-511891 A | 3/2009 |
| JP | 2009-527733 A | 7/2009 |
| JP | 2009-533673 A | 9/2009 |

(Continued)

OTHER PUBLICATIONS

"Electron Excitation on Surface", (1996), pp. 144-155 with English translation.

(Continued)

*Primary Examiner* — Abdullahi Nur
(74) *Attorney, Agent, or Firm* — Harness, Dickey & Pierce, P.L.C.

(57) ABSTRACT

A Raman spectroscopic apparatus analyzes a substance under analysis and includes a light source that emits light of a first wavelength, an optical device that adsorbs the substance under analysis and is irradiated with the light of the first wavelength, and an optical detector that receives light radiated from the optical device. The optical device includes a first structural member that generates charge transfer resonance in response to the light of the first wavelength and a second structural member that is less than or equal to 5 nm from the first structural member and generates surface plasmon resonance in response to the light of the first wavelength. The first structural member is made of a metal or a semiconductor, and the second structural member is made of a metal different from the material of the first structural member.

20 Claims, 14 Drawing Sheets

(56) References Cited

U.S. PATENT DOCUMENTS

2009/0097023 A1  4/2009  Gilbert
2009/0273778 A1  11/2009  Neerken et al.

FOREIGN PATENT DOCUMENTS

| | | |
|---|---|---|
| JP | 4806411 B2 | 11/2011 |
| JP | 2012-229929 A | 11/2012 |
| JP | 2013-096939 A | 5/2013 |
| WO | WO-2006-098446 A1 | 9/2006 |

OTHER PUBLICATIONS

Demuth, J.E. et al., "Observation of Charge-Transfer States for Puridine Chemisorbed ON Ag", Physical Review Letters, IBM Thomas J. Watson Research Center, Yorktown Heights, NY 10598, vol. 47, No. 1, Jul. 6, 1981, pp. 57-60.

Schmeisser, D. et al., "Metal-Molecule Charge-Transfer Excitations on Silver Films", Chemical Physics Letters, IBM Research Center, Yorktown Heights, NY 10598, Oct. 156, 1981, vol. 87, No. 4, pp. 324-326.

English translation of Takase, Mai et al., "In-Situ Monitoring of Dynamic Behavior of a Single Molecule at Metal Nanogap", Faculty of Science, Hokkaido University (Nishi 8, Kita 10jyo, Kita-ku, Sapporo-shi, Hokkando 060-0810), vol. 62, No. 6, (2011), pp. 301-305.

Nie, S. et al., "Probing Single Molecules and Single Nanoparticles by Surface-Enhanced Raman Scattering", Science 275, 1102 (1997), May 25, 2009, pp. 1102-1106.

Hulteen, J.C. et al., "Nanosphere Lithography: A Materials General Fabrication Process for Periodic Particle Array Surfaces", Department of Chemistry and Materials Research Center, Northwestern University, Illinois 60208, vol. 13, No. 3, Oct. 17, 1994, pp. 1553-1558.

Sawai, Y. et al., "Observation of a Small Number of Molecules at a Metal Nanogap Arrayed on a Solid Surface Using Surface-Enhanced Raman Scattering", Division of Chemistry, Graduate School of Science, Hokkaido University, Sapporo, Hokkaido 060-0180, Japan, and NTT Basic Research Laboratories, NTT Corporation, Oct. 1, 2006, pp. 1658-1662.

\* cited by examiner

FIG. 22A
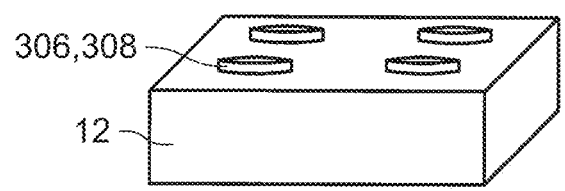
FIG. 22B
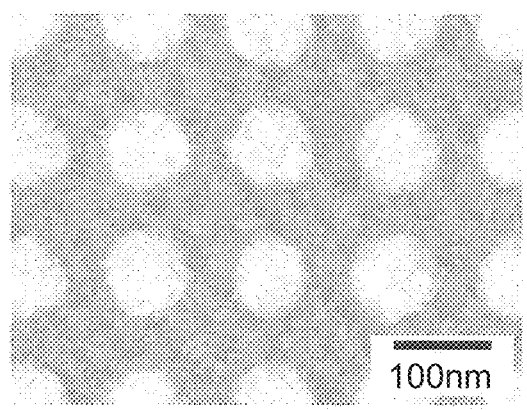
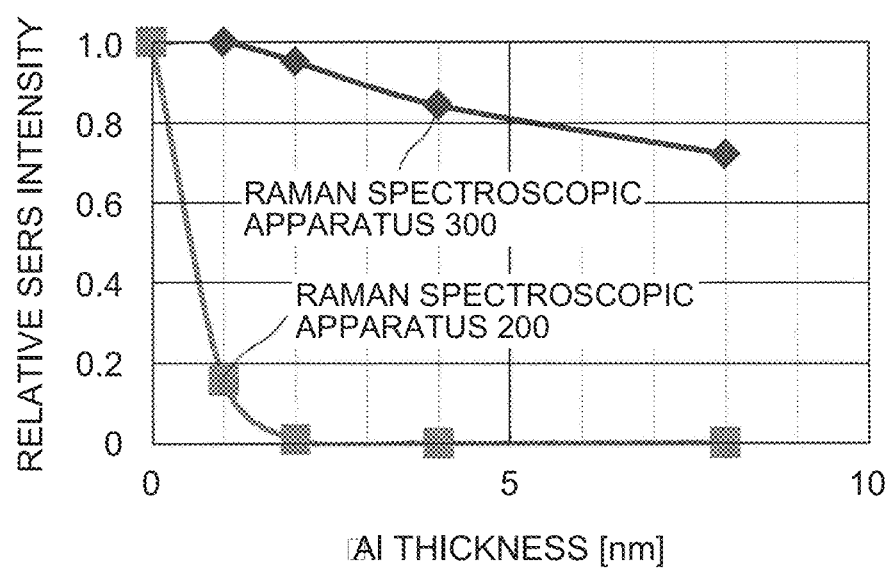
FIG. 23

RAMAN SPECTROSCOPIC APPARATUS, RAMAN SPECTROSCOPIC METHOD, AND ELECTRONIC APPARATUS

BACKGROUND

1. Technical Field

The present invention relates to a Raman spectroscopic apparatus, a Raman spectroscopic method, and an electronic apparatus.

2. Related Art

In recent years, the demand for a sensor chip (optical device) used for medical diagnosis, beverage and food inspection, and other purposes has been increasing, and the development of a highly sensitive, compact sensor chip has been desired. To meet the demand, sensor chips of a variety of types including a sensor chip using an electrochemical approach have been studied. Among them, a sensor chip using spectroscopic analysis based on surface plasmon resonance (SPR), in particular, surface enhanced Raman scattering (SERS) has received increasing attention for a variety of reasons. For example, such a sensor chip can be an integrated chip, can be manufactured at low cost, and can be used in any measurement environment.

Surface plasmon is a vibration mode of an electron wave that is coupled to light under certain surface-specific boundary conditions. To excite surface plasmon, there are a method in which a diffraction grating engraved on a metal surface is used to couple light and plasmon to each other and a method in which an evanescent wave is used. An example of a sensor chip using SPR is formed of a total reflection prism and a metal film that is formed on a surface of the prism and comes into contact with a target substance. The thus configured sensor chip detects whether or not a target substance has been adsorbed, for example, whether or not an antigen in an antigen-antibody reaction has been adsorbed.

There is propagating surface plasmon present on a metal surface, whereas there is localized surface plasmon present on a metal fine particle. It is understood that when the localized surface plasmon, that is, surface plasmon localized on a metal microstructure of a surface is excited, a significantly enhanced electric field is induced.

It is further understood that when an enhanced electric field formed by localized surface plasmon resonance (LSPR) using metal nano-particles is irradiated with Raman scattered light, a surface enhanced Raman scattering phenomenon enhances the Raman scattered light, and a highly sensitive sensor (detection device) has been proposed. Using the principle described above allows detection of trace quantities of a variety of substances.

For example, JP-A-2013-96939 describes a Raman spectroscopic apparatus including a sensor chip in which metal particles made of Ag or Au are periodically arranged.

However, the Raman spectroscopic apparatus described in JP-A-2013-96939, which has a trap film, cannot detect every target substance in a highly sensitive manner. Further, for example, a Raman spectroscopic apparatus including a sensor chip (optical device) in which metal particles made of Ag are periodically arranged can detect a molecule containing an N atom having an unpaired electron, such as pyridine and adenine, in a highly sensitive manner because Ag tends to chemically adsorb such a molecule but cannot detect a molecule not containing an N atom, such as acetone and ethanol, in a highly sensitive manner because Ag does not tend to chemically adsorb such a molecule.

SUMMARY

An advantage of some aspects of the invention is to provide a Raman spectroscopic apparatus capable of detecting Raman scattered light from a target substance in a highly sensitive manner. Another advantage of some aspects of the invention is to provide a Raman spectroscopic method that allows detection of Raman scattered light from a target substance in a highly sensitive manner. Still another advantage of some aspects of the invention is to provide an electronic apparatus including the Raman spectroscopic apparatus described above.

An aspect of the invention is directed to a Raman spectroscopic apparatus that analyzes a substance under analysis (target substance) and includes a light source that emits light of a first wavelength, an optical device that adsorbs the substance under analysis (target substance) and is irradiated with the light of the first wavelength, and an optical detector that receives light radiated from the optical device, wherein the optical device includes a first structural member that generates charge transfer resonance in response to the light of the first wavelength, and a second structural member that is disposed in a position spaced apart from the first structural member by a spacing less than or equal to 5 nm and generates surface plasmon resonance in response to the light of the first wavelength, the first structural member is made of a metal or a semiconductor, and the second structural member is made of a metal different from the material of the first structural member.

The Raman spectroscopic apparatus described above can provide a chemical enhancement effect even when the substance under analysis (target substance) is acetone or ethanol, which a Raman spectroscopic apparatus including an optical device having periodically arranged metal particles made of, for example, Ag cannot detect in a highly sensitive manner, and the resultant synergy between an electric field enhancement effect and the chemical enhancement effect allows a SERS effect to be provided. As a result, the Raman spectroscopic apparatus described above can increase the intensity of Raman scattered light and can hence detect Raman scattered light from the substance under analysis (target substance) in a highly sensitive manner.

In the Raman spectroscopic apparatus according to the aspect of the invention, the first structural member may be provided so that the first structural member coats the second structural member.

In the Raman spectroscopic apparatus described above, the optical device can be formed in simpler manufacturing steps.

In the Raman spectroscopic apparatus according to the aspect of the invention, the first structural member may be provided in a plurality of positions, the second structural member may be provided in a plurality of positions, and the plurality of second structural members may be spaced apart from each other.

In the Raman spectroscopic apparatus described above, the optical device can be formed in simpler manufacturing steps, and the electric field enhancement effect can be enhanced.

In the Raman spectroscopic apparatus according to the aspect of the invention, the plurality of first structural members may be spaced apart from each other.

The Raman spectroscopic apparatus described above can detect Raman scattered light from the substance under analysis (target substance) in a highly sensitive manner.

In the Raman spectroscopic apparatus according to the aspect of the invention, the first structural member may have a thickness less than or equal to 1 nm.

In the Raman spectroscopic apparatus described above, the electric field enhancement effect can be enhanced.

In the Raman spectroscopic apparatus according to the aspect of the invention, the second structural member may be made of Ag, Au, or Al.

In the Raman spectroscopic apparatus described above, each of Ag, Au, and Al is a metal having a dielectric constant with a small imaginary part in the visible wavelength range and can hence enhance the electric field enhancement effect.

In the Raman spectroscopic apparatus according to the aspect of the invention, the substance under analysis (target substance) may be acetone or ethanol.

The Raman spectroscopic apparatus described above can also detect a molecule not containing an N atom, such as acetone and ethanol, in a highly sensitive manner.

In the Raman spectroscopic apparatus according to the aspect of the invention, the substance under analysis (target substance) may be acetone, the first wavelength may be greater than or equal to 500 nm but less than or equal to 700 nm, and the second structural member may have a size greater than or equal to 40 nm but less than or equal to 75 nm.

The Raman spectroscopic apparatus described above allows the wavelength band where the electric field enhancement effect can be enhanced and the wavelength band where the chemical enhancement effect can be enhanced to coincide with each other. As a result, synergy between the electric field enhancement effect and the chemical enhancement effect can be more reliably obtained.

The Raman spectroscopic apparatus according to the aspect of the invention may further include a light source that irradiates the substance under analysis (target substance) with light of a second wavelength having energy corresponding to the difference in energy between a ground state and a minimally excited state of the substance under analysis (target substance).

In the Raman spectroscopic apparatus described above, the reaction in which the first structural member adsorbs the substance under analysis (target substance) is encouraged, whereby the chemical enhancement effect can be enhanced.

Another aspect of the invention is directed to a Raman spectroscopic method including irradiating an optical device that adsorbs a substance under analysis (target substance) with light of a first wavelength and receiving light radiated from the optical device for analysis of the substance under analysis (target substance), wherein the optical device includes a first structural member that generates charge transfer resonance in response to the light of the first wavelength, and a second structural member that is disposed in a position spaced apart from the first structural member by a spacing less than or equal to 5 nm and generates surface plasmon resonance in response to the light of the first wavelength, the first structural member is made of a metal or a semiconductor, and the second structural member is made of a metal different from the material of the first structural member.

The Raman spectroscopic method described above allows highly sensitive detection of Raman scattered light from the substance under analysis (target substance).

Still another aspect of the invention is directed to an electronic apparatus including the Raman spectroscopic apparatus according to the aspect of the invention, a computation unit that computes health care information based on detected information from the optical detector, a storage unit that stores the health care information, and a display unit that displays the health care information.

The electronic apparatus described above, which includes the Raman spectroscopic apparatus according to the aspect of the invention, can readily detect a trace quantity of substance and provide highly precise health care information.

In the electronic apparatus according to the aspect of the invention, the health care information may include information on whether or not there is at least one type of biological substance selected from the group including bacteria, viruses, proteins, nucleic acids, and antigens and antibodies or at least one type of compound selected from inorganic molecules and organic molecules or information on the amount thereof.

The electronic apparatus described above can readily detect a trace quantity of substance and provide highly precise health care information.

Yet another aspect of the invention is directed to a Raman spectroscopic apparatus that analyzes a substance under analysis (target substance) and includes a light source that emits light of a first wavelength, an optical device that adsorbs the substance under analysis (target substance) and is irradiated with the light of the first wavelength, and an optical detector that receives light radiated from the optical device, wherein the optical device includes a substrate, a first structural member that is formed on the substrate and generates charge transfer resonance in response to the light of the first wavelength, and a second structural member that is formed on the substrate, is disposed in a position spaced apart from the first structural member by a spacing less than or equal to 5 nm, and generates surface plasmon resonance in response to the light of the first wavelength, the first structural member is made of a metal or a semiconductor, and the second structural member is made of a metal different from the material of the first structural member.

The Raman spectroscopic apparatus described above can provide the chemical enhancement effect even when the substance under analysis (target substance) is acetone or ethanol, which a Raman spectroscopic apparatus including an optical device having periodically arranged metal particles made of, for example, Ag cannot detect in a highly sensitive manner, and the resultant synergy between the electric field enhancement effect and the chemical enhancement effect allows a SERS effect to be provided. As a result, the Raman spectroscopic apparatus described above can increase the intensity of Raman scattered light and can hence detect Raman scattered light from the substance under analysis (target substance) in a highly sensitive manner.

BRIEF DESCRIPTION OF THE DRAWINGS

Embodiments of the invention will be described with reference to the accompanying drawings, wherein like numbers reference like elements.

FIG. 22A is a perspective view diagrammatically showing another step of manufacturing the Raman spectroscopic apparatus according to the second variation of the present embodiment, and FIG. 22B is a SEM photograph showing the manufacturing step.

FIG. 23 shows graphs illustrating the relationship between Al thickness and relative SERS intensity.

DESCRIPTION OF EXEMPLARY EMBODIMENTS

A preferred embodiment of the invention will be described below in detail with reference to the drawings. The embodiment that will be described below is not intended to unduly limit the scope of the invention set forth in the appended claims. Further, all the configurations that will be described below are not necessarily essential configuration requirements of the invention.

1. RAMAN SPECTROSCOPIC APPARATUS

Figure 1:
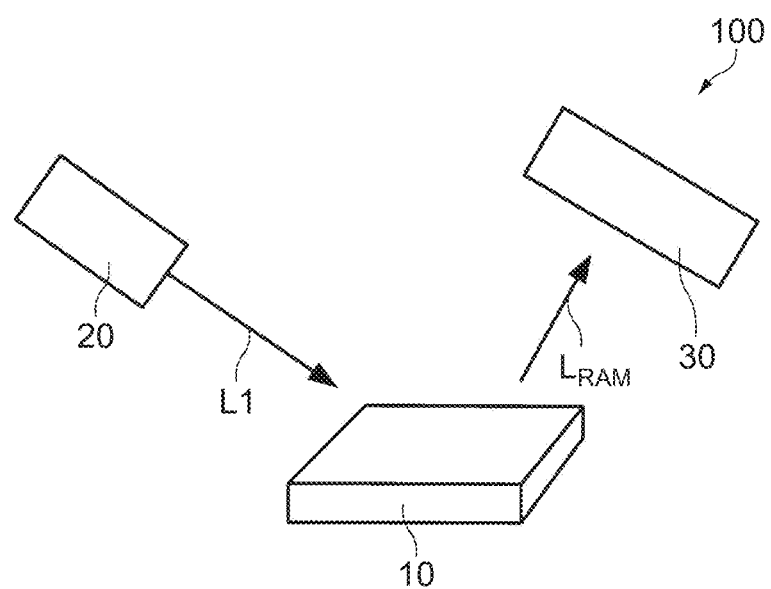
FIG. 1 diagrammatically shows a Raman spectroscopic apparatus according to an embodiment of the invention.

A Raman spectroscopic apparatus according to an embodiment of the invention will first be described with reference to the drawings. FIG. 1 diagrammatically shows a Raman spectroscopic apparatus 100 according to the present embodiment.

The Raman spectroscopic apparatus 100 includes an optical device (sensor chip) 10, a light source 20, and an optical detector 30, as shown in FIG. 1. The Raman spectroscopic apparatus 100 detects and analyzes (qualitatively analyzes or quantitatively analyzes) Raman scattered light from a target substance. The optical device 10, the light source 20, and the optical detector 30 will be sequentially described below.

1.1. Optical Device

Figure 2:
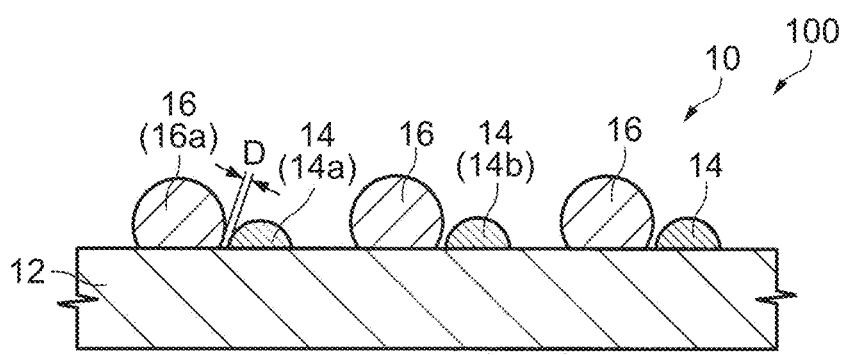
FIG. 2 is a cross-sectional view diagrammatically showing an optical device of the Raman spectroscopic apparatus according to the present embodiment.

FIG. 2 is a cross-sectional view diagrammatically showing the optical device 10 of the Raman spectroscopic apparatus 100 according to the present embodiment. The optical device 10 includes a substrate 12, first structural members 14, and second structural members 16, as shown in FIG. 2. The optical device 10 adsorbs a target substance and is irradiated with light L1 of a first wavelength emitted from the light source 20.

The substrate 12 is, for example, a glass substrate. Although not shown, a metal layer may be provided on the lower surface of the substrate 12.

The first structural members 14 are provided on the substrate 12. The shape of the first structural members 14 is not limited to a specific shape, and the first structural members 14 in the example shown in FIG. 2 have a semicircular cross-sectional shape. The structural members 14 may have a circular shape in a plan view. The first structural members 14 may instead have a cylindrical shape. The first structural members 14 have a thickness, for example, greater than or equal to 0.5 nm but less than or equal to 30 nm. The first structural members 14 have a size (the size in a plan view, the diameter in the case where the shape in a plan view is a circle), for example, greater than or equal to 0.5 nm but less than or equal to 80 nm. The first structural members 14 are disposed in a plurality of positions in correspondence with the second structural members 16. The spacing (e.g., distance) between adjacent first structural members 14 is, for example, greater than or equal to 1 nm but less than or equal to 100 nm.

The first structural members 14 are made of a metal. The first structural members 14 are preferably made of, for example, Al, Ag, Au, or Cu.

The first structural members 14 adsorb a target substance (target molecule) that is not shown. The term "adsorb" used herein is a phenomenon in which the concentration of the target substance in a portion on a boundary surface of an object increases with respect to the concentration thereof in the surrounding portion, specifically, is chemical adsorption based on covalent bond/coordinate bond. When the target substance is irradiated with the light L1 of the first wavelength (incident light), generated scattered light contains Raman scattered light L of a wavelength different from the first wavelength of the light L1 (see FIG. 1). The wavelength of the Raman scattered light L corresponds to specific vibration energy according to the structure of the target substance. Measuring the wavelength of the Raman scattered light L therefore allows identification of the target substance. The target substance is, for example, acetone or ethanol.

Figure 3:
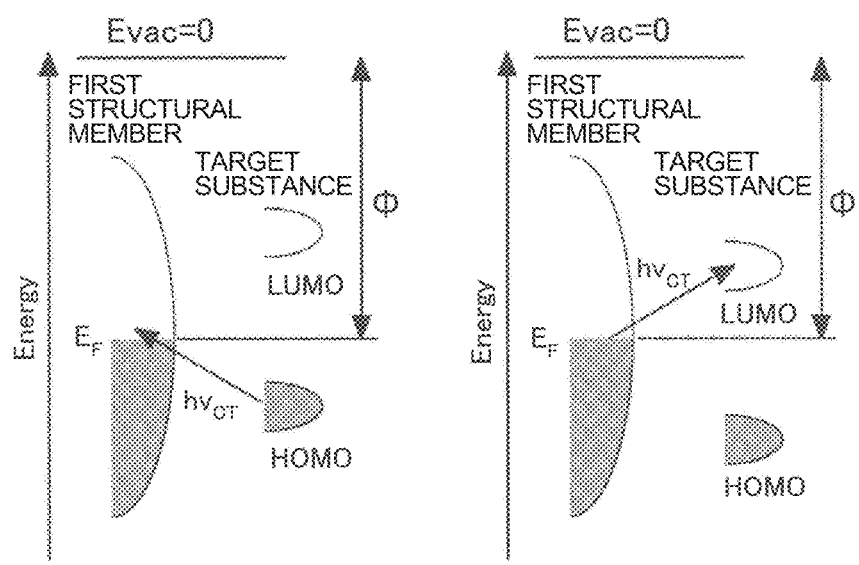
FIG. 3 describes charge transfer resonance.

The first structural members 14, when they adsorb the target substance, generate charge transfer (CT) resonance in response to the light L1 of the first wavelength. FIG. 3 describes the charge transfer resonance. In FIG. 3, Evac represents the vacuum level, and Φ represents the work function of each of the first structural members 14.

When the surface of each of the first structural members 14 (Al, for example) adsorbs a target substance (acetone, for example), the molecular orbital of acetone and the electronic orbital of Al interact with each other to produce an Al-acetone complex. At this point, a Fermi level ($E_F$) is present in the Al, and a difference in energy ($hv_{CT}$) ranging from 1 to 4 eV is created between the Fermi level in the Al and a HOMO (highest occupied molecular orbital) level or a LUMO (lowest unoccupied molecular orbital) level in an acetone molecule. When the Al-acetone complex is irradiated with light having energy ranging from 1 to 4 eV ($hv_{CT}$), charge transfer optical absorption (CT absorption) occurs in the Al-acetone complex, followed by excitation between the HOMO level and the Fermi level or between the Fermi level and the LUMO level, which is called "charge transfer (CT) resonance (charge transfer transition)." The energy band where the CT resonance occurs is called a CT level, which can be identified by measuring an electron spectrum.

The Al-acetone complex that generates the CT resonance provides a resonance Raman effect. The "resonance Raman effect" is a phenomenon in which a Raman scattering cross-sectional area increases by a factor of $10^2$ to $10^4$ when the excitation wavelength is a wavelength having energy corresponding to an electronic transition absorption band. When a hybrid orbital level formed when a metal chemically adsorbs a molecule has an energy-wise width as described above, the molecule is more likely to transition to an excited state, resulting in enhancement of Raman scattered light, which is called a "chemical enhancement effect." The chemical enhancement effect is provided only when the surface of any of the first structural members 14 adsorbs a target substance.

The second structural members 16 are provided on the substrate 12, as shown in FIG. 2. The shape of the second structural members 16 is not limited to a specific shape, but the size of the second structural members 16 (the size in a plan view, the diameter in a case where the shape in a plan view is a circle) is smaller than or equal to the first wavelength of the light L1 emitted from the light source 20. The second structural members 16 may have a cylindrical shape. The size of the second structural members 16 is greater than or equal to 40 nm but less than or equal to 75 nm and is more preferably 50 nm. The second structural members 16 preferably have a thickness, for example, greater than or equal to 5 nm but less than or equal to 100 nm. The second structural members 16 are provided in a plurality of positions. In the example shown in FIG. 2, the plurality of second structural members 16 are periodically disposed. The spacing (e.g., distance) between adjacent second structural members 16 is, for example, greater than or equal to 1 nm but less than or equal to 100 nm.

The second structural members 16 are made of a metal that is different from the material (e.g., the metal material) of the first structural members 14. Preferably, the second structural members 16 are made of, for example, Ag, Au, or Al. For example, the first structural members 14 are made of Al, and the second structural members 16 are made of Ag.

The second structural members 16 generate surface plasmon resonance (SPR) in response to the light L1 of the first wavelength emitted from the light source 20. Specifically, the second structural members 16 generate localized surface plasmon resonance (LSPR) in response to the light L1 of the first wavelength. "LSPR" is a phenomenon in which when light is incident on a metal microstructure smaller than or equal to the wavelength of the light (second structural members 16), the electric field component of the light collectively vibrates free electrons present in the metal so that a localized electric field is induced in a space outside the metal. The localized electric field can enhance Raman scattered light. The enhancement of Raman scattered light under an electric field induced by SPR as described above is called an "electric field enhancement effect."

The second structural members 16 are disposed so that they are spaced apart from the first structural members 14 by a spacing D, which is 5 nm or less. The spacing D may be zero (D=0). That is, the second structural members 16 may be provided so that they are in contact with the first structural members 14.

The sentence "The second structural members are disposed so that they are spaced apart from the first structural members by a spacing, which is 5 nm or less" means that each of the second structural members 16 is spaced apart from the first structural member 14 that is closest thereto by 5 nm or less. That is, the spacing between a second structural members 16a and a first structural members 14a is 5 nm or less as shown in FIG. 2, but the spacing between the second structural member 16a and a first structural member 14b may not be 5 nm or less.

When the spacing D between the second structural members 16 and the first structural members 14 is set at 5 nm or less, synergy between the electric field enhancement effect and the chemical enhancement effect allows the optical device 10 to provide a surface enhanced Raman scattering spectroscopy (SERS) effect. The intensity of the Raman scattered light $L_{RAM}$ can therefore be increased. It is noted that the magnitude of a localized electric field (hotsite) induced by LSPR is maximized on the surface of each of the second structural members 16 and exponentially decreases with distance from the surface of the second structural member 16. When the spacing between the first structural members and the second structural members is greater than 5 nm, no synergy between the electric field enhancement effect and the chemical enhancement effect can be provided. In this case, the intensity of the Raman scattered light $L_{RAM}$ cannot be sufficiently increased.

1.2. Light Source

The light source 20 emits the light L1 of the first wavelength, as shown in FIG. 1. The light source 20 is, for example, a semiconductor laser, and the light L1 of the first wavelength is laser light. The first wavelength of the light L1 is not limited to a specific value and is, for example, greater than or equal to 500 nm but less than or equal to 700 nm and is more preferably 632 nm. The light L1 of the first wavelength causes a complex of the first structural members 14 and the target substance (Al-acetone complex, for example) that is produced when the first structural members 14 adsorbs the target substance to generate CT resonance. Further, the light L1 of the first wavelength causes the second structural members 16 to generate LSPR.

1.3. Optical Detector

The optical detector 30 receives light radiated from the optical device 10. Specifically, the optical detector 30 receives the Raman scattered light (SERS light) $L_{RAM}$ radiated from the optical device 10 (enhanced by optical device 10). The optical detector 30 may be formed, for example, of a CCD (charge coupled device), a photomultiplier, a photodiode, or an imaging plate.

1.4. Specific Configuration of Raman Spectroscopic Apparatus

Figure 4:
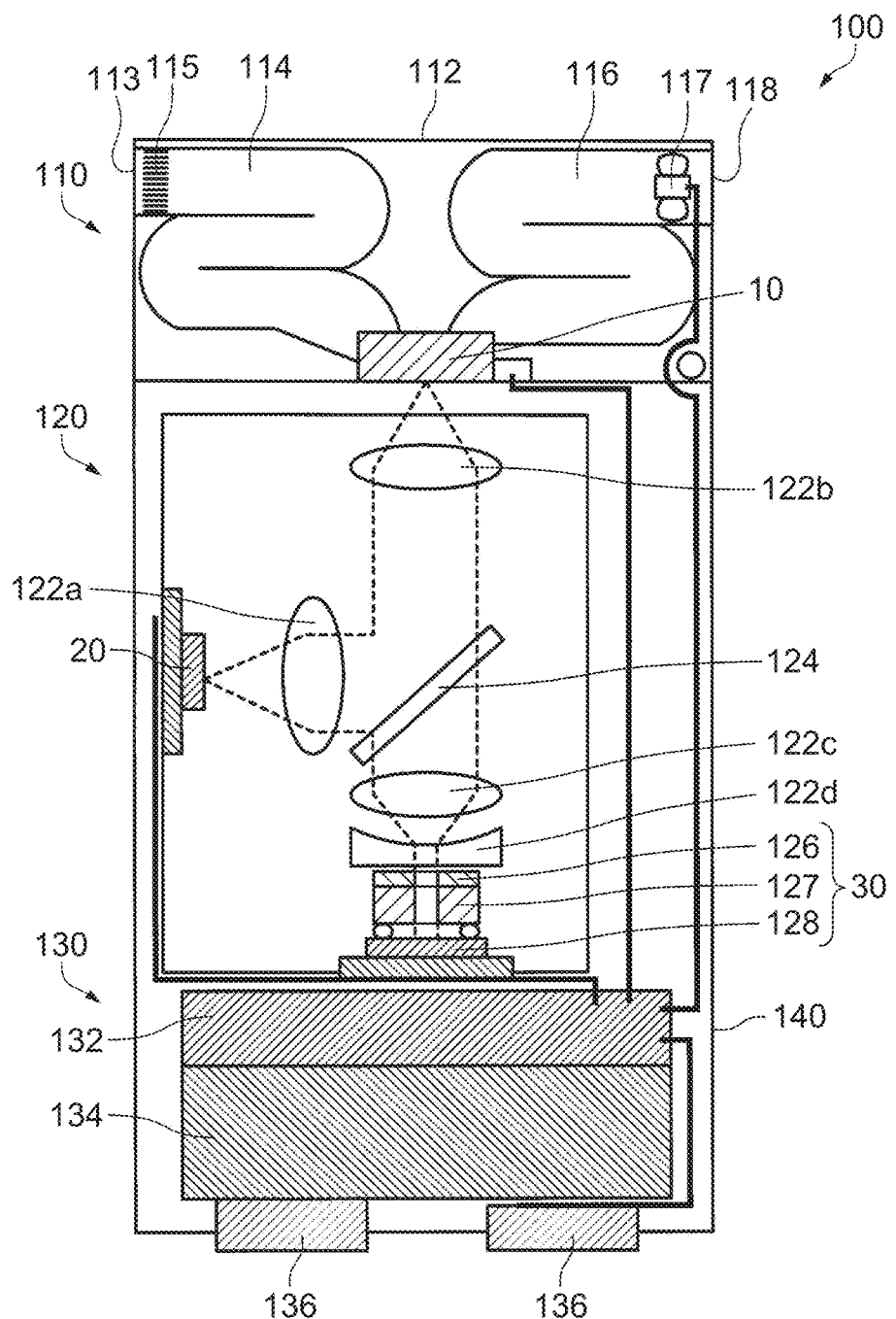
FIG. 4 diagrammatically shows a specific configuration of the Raman spectroscopic apparatus according to the present embodiment.

A specific configuration of the Raman spectroscopic apparatus 100 will be described. FIG. 4 diagrammatically shows a specific configuration of the Raman spectroscopic apparatus 100 according to the present embodiment.

The Raman spectroscopic apparatus 100 includes a gas specimen holder 110, a detection section 120, a controller 130, an enclosure 140, which accommodates the detection section 120 and the controller 130, as shown in FIG. 4.

The gas specimen holder 110 includes the optical device 10, a cover 112, which covers the optical device 10, a suction channel 114, and a discharge channel 116. The detection section 120 includes the light source 20, lenses 122*a*, 122*b*, 122*c*, and 122*d*, a half-silvered mirror 124, and the optical detector 30. The controller 130 includes a detection controller 132, which processes a detection signal from the optical detector 30 to control the detection section 120, and an electric power controller 134, which controls (supplies) electric power for the light source 20 and other components. The controller 130 may be electrically connected to connection sections 136, which connects the controller 130 to an external apparatus, as shown in FIG. 4.

In the Raman spectroscopic apparatus 100, when a suction mechanism 117 provided in the discharge channel 116 is operated, the pressure in the suction channel 114 and the discharge channel 116 goes negative, whereby a gas specimen containing a target substance to be detected is sucked through a suction port 113. A dust removal filter 115 is provided at the suction port 113 and can remove relatively large dust, part of water vapor, and other unwanted substances. The gas specimen passes through the suction channel 114, a portion in the vicinity of the optical device 10, and the discharge channel 116 and is discharged through a discharge port 118. When the gas specimen passes through the portion in the vicinity of the optical device 10, the target substance is adsorbed by the surface of the optical device 10 and detected by the optical device 10.

The suction channel 114 and the discharge channel 116 are so shaped that no external light is incident on the optical device 10. The shape prevents light that generates noise that is not related to Raman scattered light from entering, whereby a signal having an improved S/N ratio can be produced. The channels 114 and 116 are, for example, made of a material that suppresses light reflection and so colored that light reflection is suppressed.

Further, the suction channel 114 and the discharge channel 116 are so shaped that fluid resistance acting on the gas specimen decreases, which allows highly sensitive detection. For example, when the channels 114 and 116 are so shaped that they have a minimum number of angled portions and hence have a smooth shape, few angled portions block the gap specimen. The suction mechanism 117 is, for example, a fan motor or a pump that provides a static pressure and a flow rate according to channel resistance.

In the Raman spectroscopic apparatus 100, the optical device 10 is irradiated with the light from the single-wavelength light source (laser light source) 20. The light emitted from the light source 20 is collected by the lens 122*a*, travels via the half-silvered mirror 124 and the lens 122*b*, and is incident on the optical device 10. The optical device 10 then radiates SERS light, which passes through the lens 122*b*, the half-silvered mirror 124, and the lenses 122*c* and 122*d*, and reaches the optical detector 30. Since the SERS light contains Rayleigh light of the same wavelength as the wavelength of the incident light from the light source 20, a filter 126 is provided in the optical detector 30 and removes the Rayleigh light. The light from which the Rayleigh light has been removed is received by a light reception device 128 via a spectrometer 127 in the optical detector 30.

The spectrometer 127 in the optical detector 30 is formed, for example, of an etalon using Fabry-Perot resonance and can change the wavelength band of light that the spectrometer 127 transmits. The light reception device 128 in the optical detector 30 provides a Raman spectrum specific to the target substance, and the resultant Raman spectrum can be compared with data held in advance for detection of the intensity of a signal from the target substance.

The Raman spectroscopic apparatus 100 is not limited to the configuration described above and may be any other apparatus that includes the optical device 10, the light source 20, and the optical detector 30 and can cause the optical device 10 to adsorb a target substance and acquire the resultant Raman scattered light.

The Raman spectroscopic apparatus 100, for example, has the following characteristics.

In the Raman spectroscopic apparatus 100, the optical device 10 includes the first structural members 14, which adsorb a target substance and generate charge transfer resonance in response to the light L1 of the first wavelength, and the second structural members 16, which are disposed so that they are spaced apart from the first structural members 14 by the spacing D, which is 5 nm or less, and generate surface plasmon resonance in response to the light L1 of the first wavelength. The first structural members 14 are made of a metal, and the second structural members 16 are made of a metal different from the material of the first structural members 14. In the thus configured Raman spectroscopic apparatus 100, appropriate selection of the materials of the first structural members 14 and the second structural members 16 in accordance with a target substance allows the light L1 of the first wavelength to exert a chemical enhancement effect based on CT resonance and an electric field enhancement effect based on LSPR. More specifically, the Raman spectroscopic apparatus 100 can provide the chemical enhancement effect even when the target substance is acetone or ethanol, which a Raman spectroscopic apparatus including an optical device having periodically arranged metal particles made of, for example, Ag cannot detect in a highly sensitive manner (cannot provide chemical enhancement effect), and the resultant synergy between the electric field enhancement effect and the chemical enhancement effect allows a SERS effect to be provided (see Experimental Examples that will be described later for details). As a result, the Raman spectroscopic apparatus 100 can increase the intensity of the Raman scattered light L and can hence detect the Raman scattered light from the target substance in a highly sensitive manner. Specifically, the Raman spectroscopic apparatus 100 can detect acetone and ethanol at a resolution of ppb (parts per billion).

In the Raman spectroscopic apparatus 100, the second structural members 16 are made of Ag, Au, or Al. Each of Ag, Au, and Al is a metal having a dielectric constant with a small imaginary part in the visible wavelength range and can hence enhance the electric field enhancement effect.

In the Raman spectroscopic apparatus 100, the target substance is acetone or ethanol. The Raman spectroscopic apparatus 100 can also detect a molecule not containing an N atom, such as acetone and ethanol, in a highly sensitive manner.

In the Raman spectroscopic apparatus 100, the target substance is acetone. The first wavelength is greater than or equal to 500 nm but less than or equal to 700 nm, and the size of the second structural members is greater than or equal to 40 nm but less than or equal to 75 nm. The Raman spectroscopic apparatus 100 therefore allows the wavelength band where the electric field enhancement effect can be enhanced and the wavelength band where the chemical enhancement effect can be enhanced to coincide with each other. As a result, synergy between the electric field enhancement effect and the chemical enhancement effect can be more reliably obtained (see Experimental Examples that will be described later for details).

As described above, in the Raman spectroscopic apparatus 100, the material of the second structural members 16 can be so selected in accordance with the wavelength band where the CT level of a target substance is present that the wavelength band where the electric field enhancement effect can be enhanced and the wavelength band where the chemical enhancement effect can be enhanced coincide with each other. For example, when the wavelength band where the CT level is present ranges from 300 to 400 nm, Al is used. When the wavelength band ranges from 400 to 700 nm, Ag is used. When the wavelength band is 700 nm and greater, Au is used.

2. METHOD FOR MANUFACTURING RAMAN SPECTROSCOPIC APPARATUS

A method for manufacturing the Raman spectroscopic apparatus 100 according to the present embodiment will be described next.

The optical device 10 is formed based, for example, on a nanosphere lithography (NSL) technology. Preferably, polystyrene (PS) beads each having a diameter of about 350 nm are mixed with ethanol, and the bead-containing ethanol is gently dripped into a beaker that contains pure water. The dripped ethanol is mixed with the pure water layer, whereas the PS beads spread over the gas-liquid interface. The substrate 12 is then gently placed on the gas-liquid interface to lift up the PS beads. A PS-filled substrate having a PS bead monolayer in which the PS beads are arranged in a closest-packed pattern is thus produced.

The PS-filled substrate then undergoes AR-NSL (angle resolved nanosphere lithography). "AR-NSL" is a metal evaporation method performed at least twice at different metal evaporation angles by using the PS beads in the PS-filled substrate as a mask. For example, the first structural members 14 are formed by performing oblique evaporation in a direction inclined by 20° to a normal to the upper surface of the substrate 12 toward one side of the normal. The second structural members 16 are then formed by performing oblique evaporation in a direction inclined by 20° to the normal to the upper surface of the substrate 12 toward the other side of the normal.

The PS beads are then removed. The PS beads are removed, for example, by causing them to undergo ultrasonic processing in water.

The optical device 10 can be formed by carrying out the steps described above.

The optical device 10, the light source 20, and the optical detector 30 are then placed in predetermined positions. The Raman spectroscopic apparatus 100 can thus be manufactured.

3. RAMAN SPECTROSCOPIC METHOD

A Raman spectroscopic method according to the present embodiment will be described next. In the Raman spectroscopic method according to the present embodiment, the optical device that has adsorbed a target substance is irradiated with the light of the first wavelength, and light radiated from the optical device is received, followed by analysis of the target substance. Preferably, the Raman spectroscopic method according to the present embodiment is performed by using the Raman spectroscopic apparatus 100. The above description of the Raman spectroscopic apparatus 100 can therefore be applied to the description of the Raman spectroscopic method according to the present embodiment. No detailed description of the Raman spectroscopic method according to the present embodiment will therefore be made.

4. EXPERIMENTAL EXAMPLES

Experimental Examples will be shown below for more specific description of the invention. The following Experimental Examples are not intended to limit the invention in any sense.

4.1. First Experiment

4.1.1. CT Level Measurement

1. Measurement System

Surface differential reflection spectroscopy (SDRS) was used to measure a CT level in a case where a metal (first structural members) adsorbs a target substance in an atmospheric environment.

Figure 5:
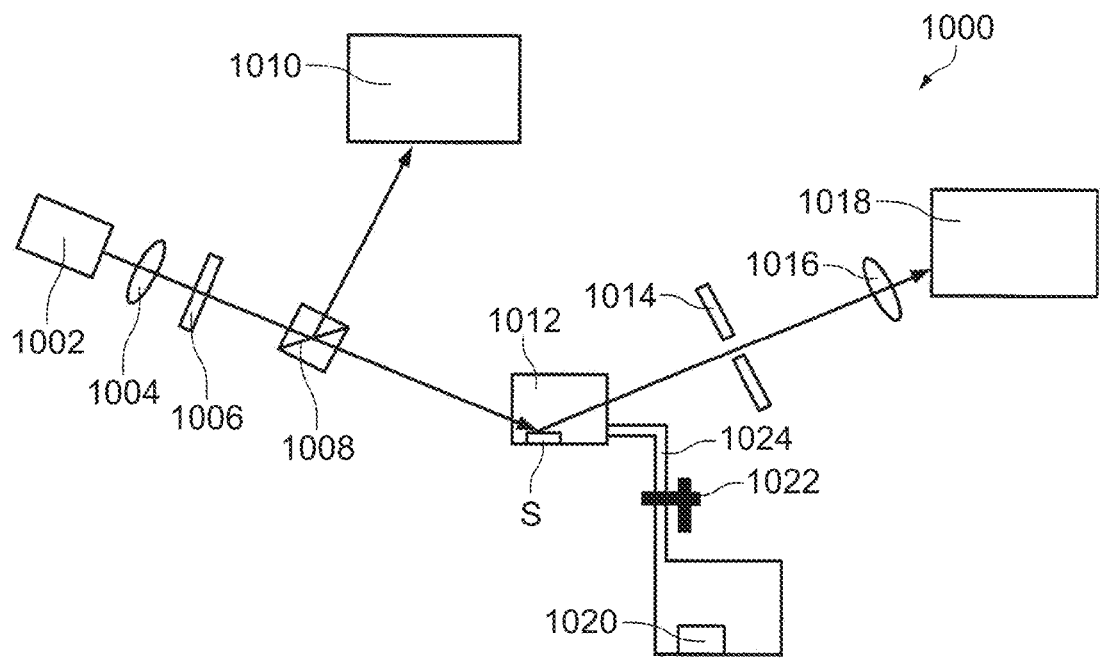
FIG. 5 diagrammatically shows an SDRS measurement system.

FIG. 5 diagrammatically shows an SDRS measurement system 1000. Light emitted from a white light source 1002 is parallelized by a lens 1004 and passes through a polarizer 1006, which converts the light into P-polarized light, as shown in FIG. 5. A beam splitter 1008 splits the light from the white light source 1002 into two, and one of the split light fluxes is used as reference light by a spectrometer 1010 to measure fluctuation of the intensity of the light from the light source. The other one of the split light fluxes is used to measure a specimen substrate S. The specimen substrate S is placed in a sealed cell 1012 made of transparent glass, and light reflected off the surface of the specimen substrate S passes through a pinhole 1014 and a lens 1016 and is detected by a spectrometer 1018, where the light undergoes a spectroscopic process. A tube 1024 is connected to the sealed cell 1012 and has an open/close cock 1022, which allows vapor of a target substance to be transported from a target substance vapor generator 1020.

SDRS, in which the incident light, which is P-polarized light, is allowed to be incident on the surface of the specimen substrate S at about Brewster's angle, allows measurement of an electron spectrum of the metal surface at atomic layer level sensitivity.

2. Measurement Results

Figure 6:
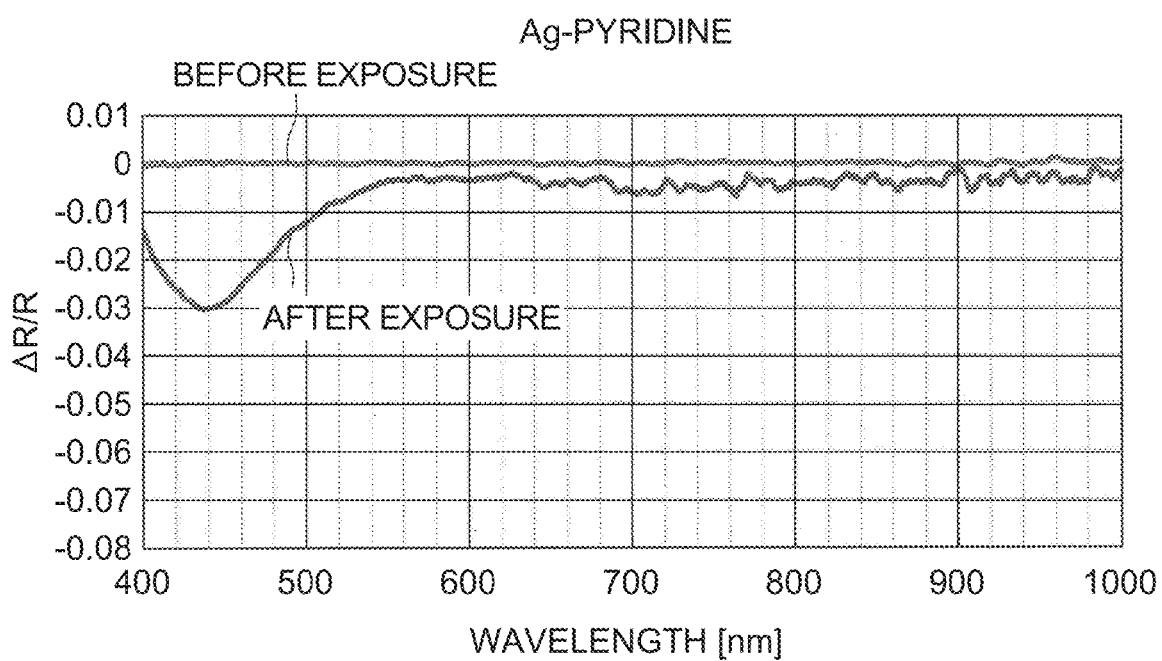
FIG. 6 shows SDRS spectra before and after pyridine vapor is exposed to an Ag surface.

In the measurement system described above, an Ag substrate was used as the specimen substrate S, and a gas-state target substance was exposed to the Ag surface for measurement of a change in the electron spectrum (SDRS spectrum) before and after the exposure. FIG. 6 shows SDRS spectra before and after pyridine vapor is exposed to the Ag surface. In FIG. 6, the horizontal axis represents the wavelength of the incident light incident on the Ag surface, and the vertical axis represents $\Delta R/R$ computed based on the following Expression (1).

$$\Delta R/R = (R - R_0)/R_0 \qquad (1)$$

In Expression (1), $R_0$ represents the reflectance before the target substance is exposed, and R represents the reflectance after the target substance is exposed.

That is, a negative $\Delta R/R$ value means that the specimen substrate S has absorbed the target substance. $R_0$ can be lowered by causing the incident light to be incident at Brewster's angle. The sensitivity can thus be increased.

The SDRS spectrum after the exposure of the pyridine has two absorption bands, unlike the SDRS spectrum before the exposure, as shown in FIG. 6. One of the two absorption bands ranges from 400 to 550 nm, and the other ranges from 600 to 1000 nm. These absorption bands show optical absorption corresponding to CT levels of an Ag-pyridine complex produced when Ag adsorbs pyridine.

Figure 7:
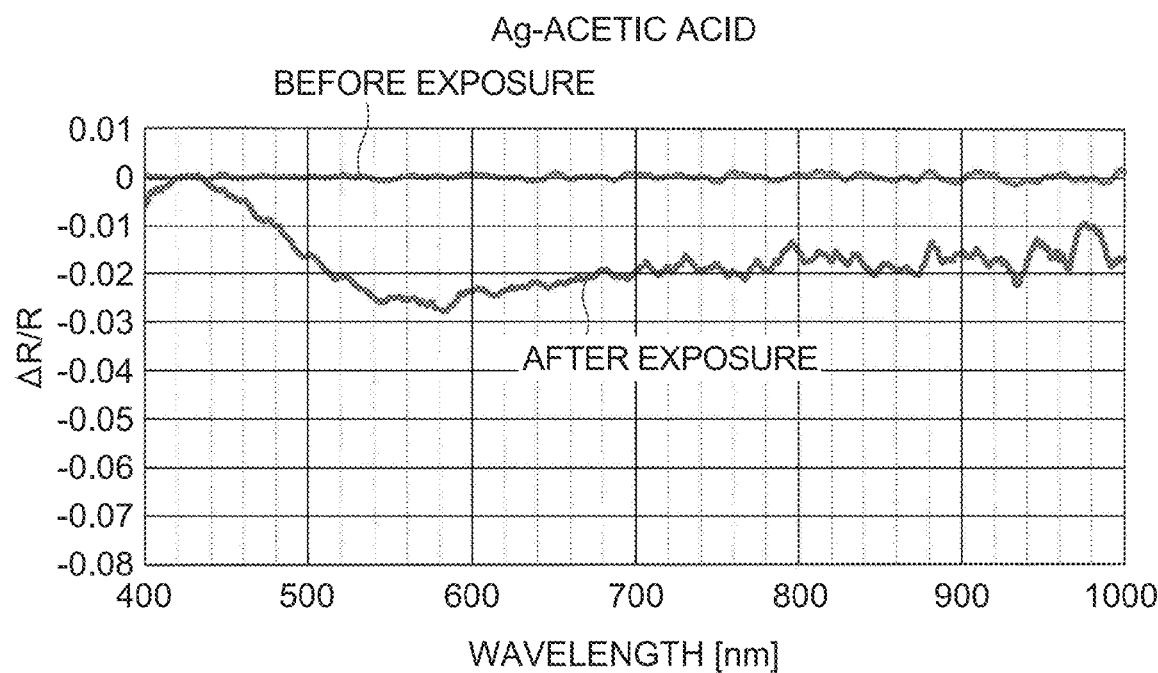
FIG. 7 shows SDRS spectra before and after acetic acid vapor is exposed to the Ag surface.

FIG. 7 shows SDRS spectra before and after acetic acid vapor is exposed to the Ag surface. The SDRS spectrum after the exposure of the acetic acid, specifically, a portion of the spectrum in the range from 440 to 1000 nm has an absorption band corresponding to a CT level, as shown in FIG. 7.

Figure 8:
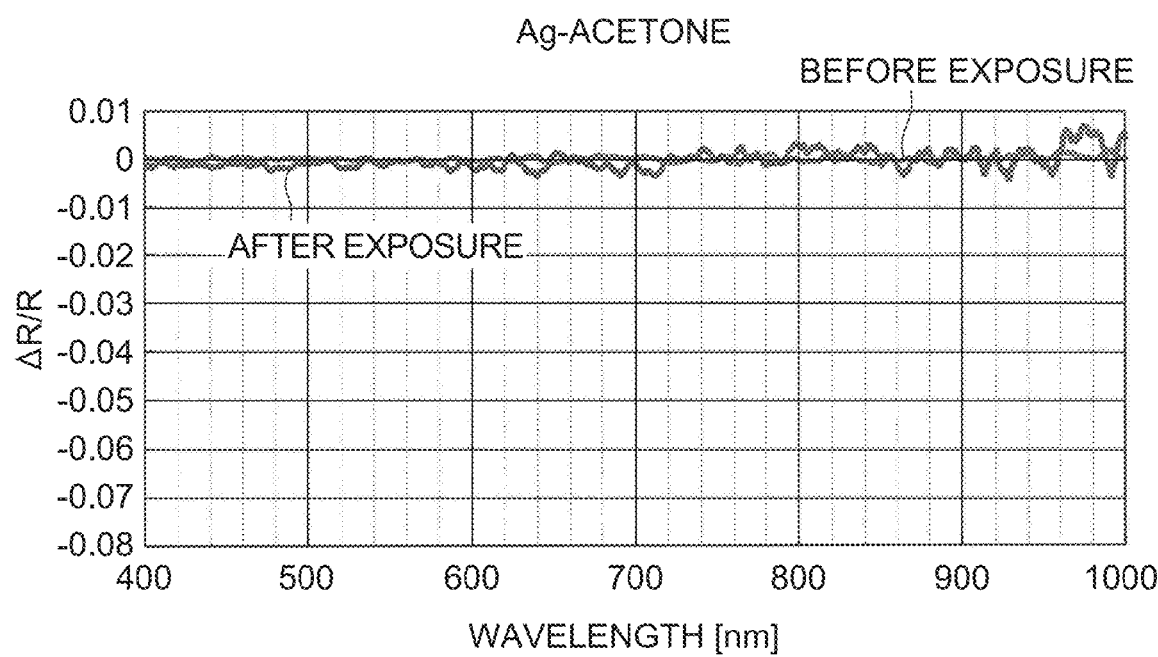
FIG. 8 shows SDRS spectra before and after acetone vapor is exposed to the Ag surface.
Figure 9:
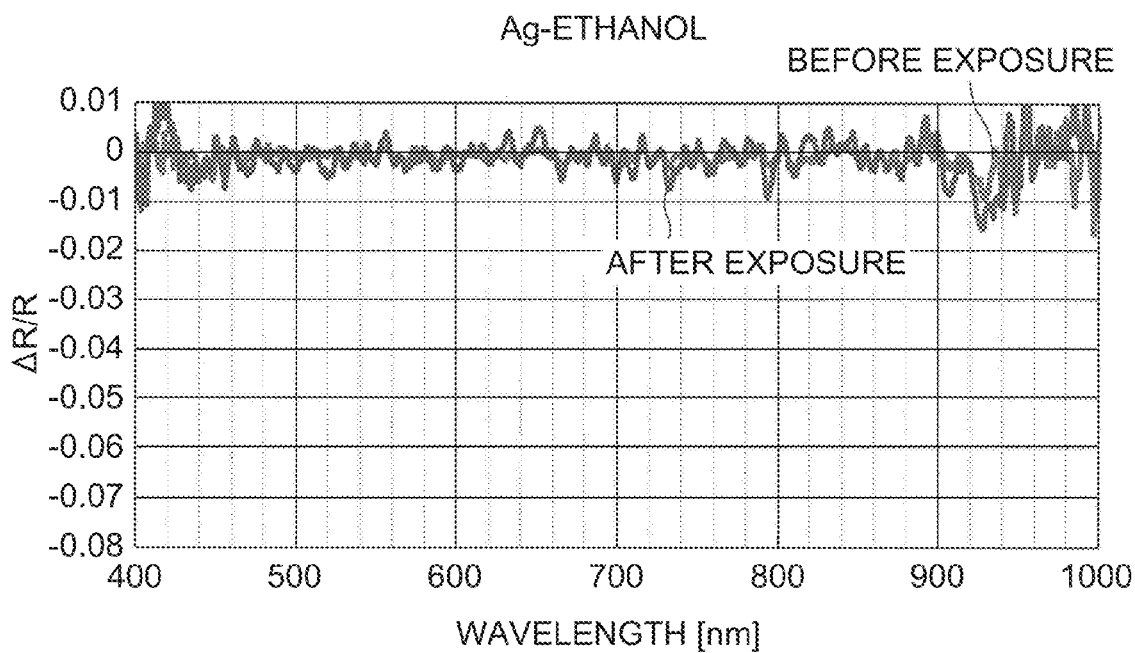
FIG. 9 shows SDRS spectra before and after ethanol vapor is exposed to the Ag surface.

FIG. 8 shows SDRS spectra before and after acetone vapor is exposed to the Ag surface. FIG. 9 shows SDRS spectra before and after ethanol vapor is exposed to the Ag surface.

The SDRS spectra of the acetone and the ethanol hardly change before and after the exposure, unlike the pyridine and the acetic acid, as shown in FIGS. 8 and 9, which means that no CT level is formed.

4.1.2. SERS Intensity Measurement

The Ag substrate was then placed in a gas-state target substance atmosphere for SERS intensity measurement. Specifically, the measurement system shown in FIG. 1 was used, in which the first wavelength of the light L1 (excitation wavelength) emitted from the light source 20 was set at 632 nm, and L was received by the optical detector 30 for SERS intensity (SERS spectrum) measurement.

Figure 10:
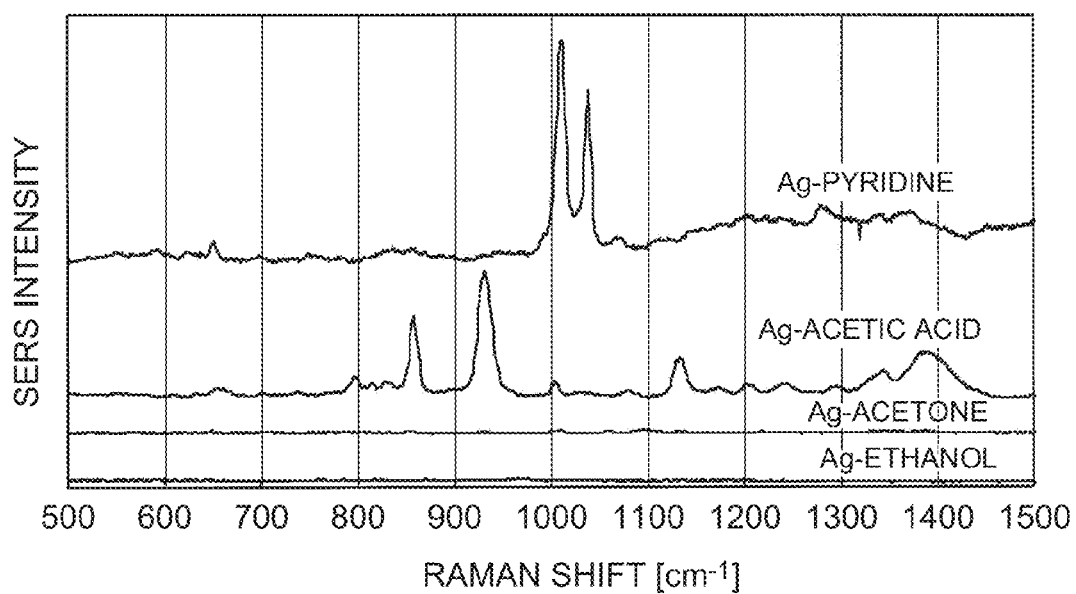
FIG. 10 shows SERS spectra in gas-state pyridine, acetic acid, acetone, and ethanol atmospheres in a case where an excitation wavelength is 632 nm.

FIG. 10 shows SERS spectra in gas-state pyridine, acetic acid, acetone, and ethanol atmospheres. The pyridine (see FIG. 6) and the acetic acid (see FIG. 7), in each of which a CT level was present at 632 nm, provided very strong signals, as shown in FIG. 10. On the other hand, the acetone (see FIG. 8) and the ethanol (see FIG. 9), in each of which no CT level was present at 632 nm, hardly provided signals, as shown in FIG. 10.

The vertical axis of FIG. 10 represents SERS relative intensity instead of absolute intensity. That is, in the example shown in FIG. 10, the Ag-pyridine complex has peaks higher than those for the Ag-acetic acid complex, which does not necessarily mean that the SERS intensity provided by the Ag-pyridine complex is greater than the SERS intensity provided by the Ag-acetic acid complex. This holds true for FIG. 13, which will be described later.

Figure 11:
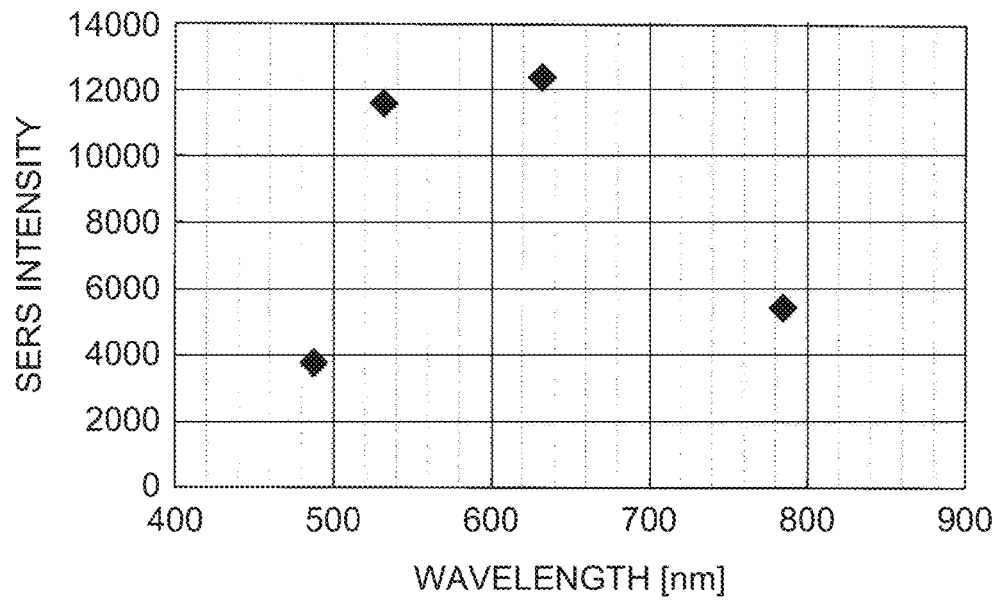
FIG. 11 shows a graph illustrating the relationship between the excitation wavelength and SERS intensity in the gas-state acetic acid atmosphere.

FIG. 11 shows a graph illustrating the relationship between the excitation wavelength and the SERS intensity in the gas-state acetic acid atmosphere. Comparison of FIG. 11 with FIG. 7 shows that the behavior of ΔR/R substantially coincides with the behavior of the SERS intensity. That is, in the wavelength band where ΔR/R has a large absolute value in FIG. 7, the SERS intensity has large values in FIG. 11. That is, it is shown that presence or absence of a CT level (presence or absence of chemical enhancement effect) results in a distinct difference in the SERS intensity.

4.2. Second Experiment

4.2.1. CT Level Measurement

An experiment for providing the chemical enhancement effect was performed in a case where acetone was used as the target substance.

Figure 12:
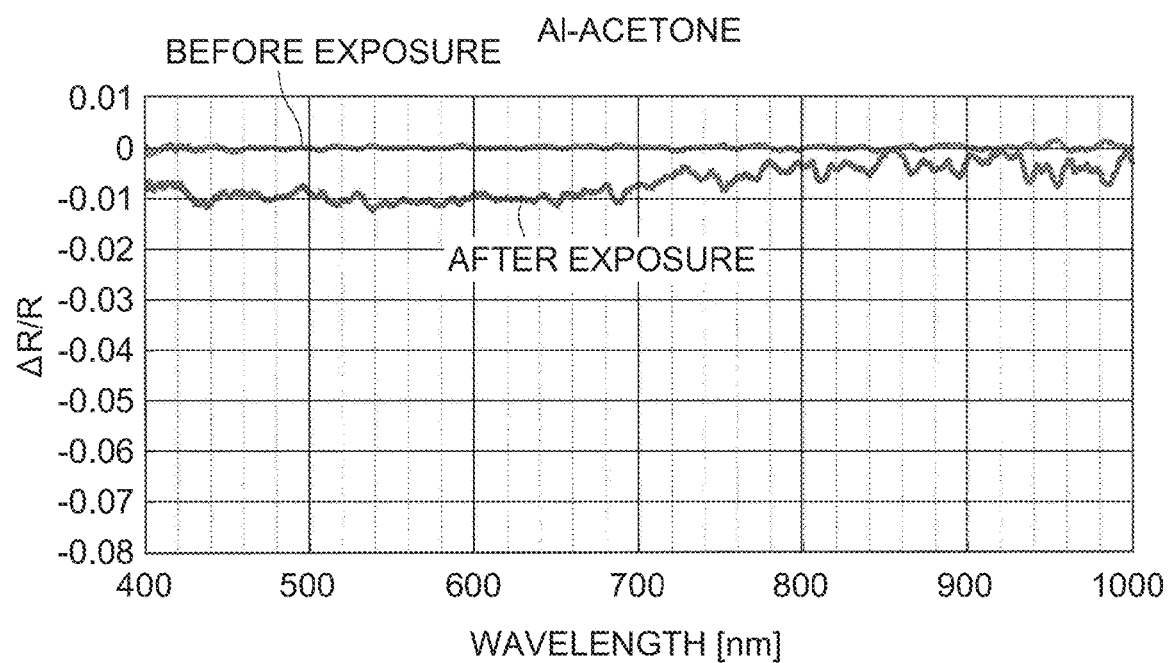
FIG. 12 shows SDRS spectra before and after acetone vapor is exposed to an Al surface.

An Al substrate (Ag substrate on which an Al film is formed to a thickness of about 1 nm) was used in place of the Ag substrate used in the first experiment for CT level measurement in the SDRS system. FIG. 12 shows spectra before and after acetone vapor is exposed to the Al surface.

The SDRS spectrum after the exposure shows that an absorption band corresponding to a CT level is present across the visible range (from 500 to 700 nm, in particular), as shown in FIG. 12. That is, it can be said that acetone, when adsorbed by Al, generates CT resonance.

4.2.2. SERS Intensity Measurement

Figure 13:
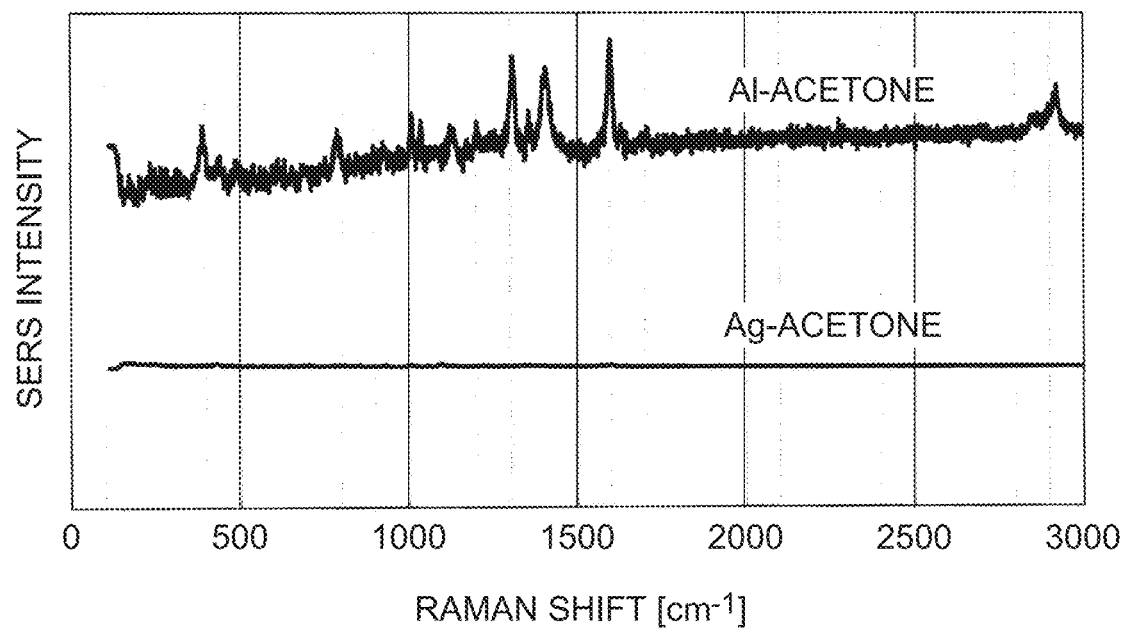
FIG. 13 shows a SERS spectrum in the gas-state acetone atmosphere in the case where the excitation wavelength is 632 nm.

The Al substrate was then placed in the gas-state acetone atmosphere for SERS intensity measurement. FIG. 13 shows a SERS spectrum in the gas-state acetone atmosphere in a case where the excitation wavelength is 632 nm. FIG. 13 further shows the SERS spectrum in the case where the Ag substrate was placed in the gas-state acetone atmosphere for comparison purposes.

In the Al substrate measurement, a distinct spectrum was detected, unlike the Ag substrate measurement, as shown in FIG. 13. That is, it is shown that even when the target substance is acetone, using first structural members made of Al allows the SERS intensity to be increased by the chemical enhancement effect based on CT resonance.

4.3. Third Experiment

Figure 14:
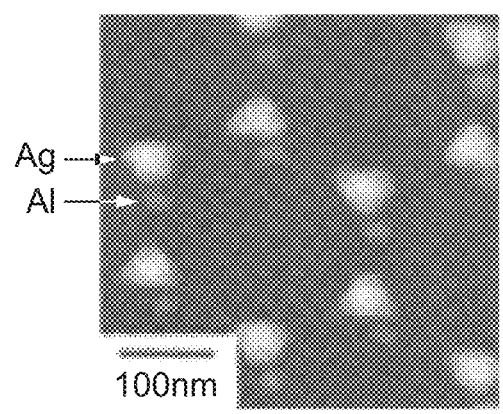
FIG. 14 is a SEM photograph of a specimen used in an experiment.

An experiment for investigating an optimum size (diameter, for example) of Ag particles (second structural members 16) was performed. A specimen (optical device) used in the present experiment was a glass substrate (substrate 12) on which Al particles (first structural members 14) and Ag particles (second structural members 16) were formed by using the NSL technology and the AR-NSL method described above. FIG. 14 is a SEM photograph of the specimen used in the present experiment. The size (size in plan view) of the Al particles was set at 20 nm. The size (size in plan view) of the Ag particles was changed among the following three levels: 50 nm; 75 nm; and 100 nm.

Figure 15:
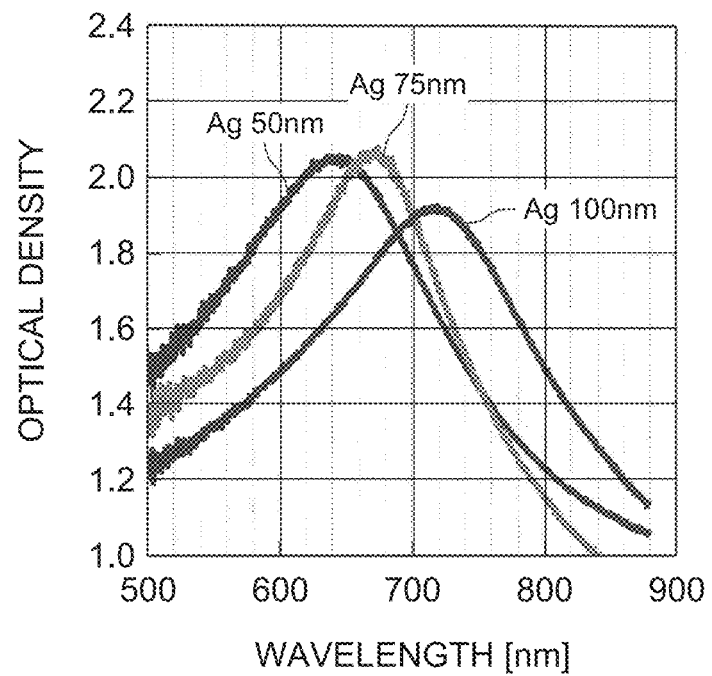
FIG. 15 shows graphs illustrating the relationship between the excitation wavelength and optical density.

FIG. 15 shows graphs illustrating the relationship between the excitation wavelength and the optical density of the specimen produced as described above. The optical density along the vertical axis of FIG. 15 is a value based on LSPR, and the greater the optical density, the greater the electric field enhancement effect provided by LSPR of the Ag particles. FIG. 15 shows that the optical density changes with the excitation wavelength.

FIG. 12 shows that, to allow the Al-acetone complex to generate CT resonance, the excitation wavelength is preferably set at a value greater than or equal to 500 nm but less than or equal to 700 nm. Therefore, setting the diameter of the Ag particles at a value greater than or equal to 40 nm but less than or equal to 75 nm and more preferably a value equal to 50 nm allows the wavelength band where the electric field enhancement effect can be enhanced based on LSPR and the wavelength band where the chemical enhancement effect can be enhanced based on CT resonance to coincide with each other, as shown in FIG. 15. As a result, synergy between the electric field enhancement effect and the chemical enhancement effect can be more reliably provided. Specifically, synergy between the electric field enhancement effect and the chemical enhancement effect at the excitation wavelength of 632 nm allows highly sensitive detection of acetone.

5. VARIATIONS OF RAMAN SPECTROSCOPIC APPARATUS

5.1. First Variation

Figure 16:
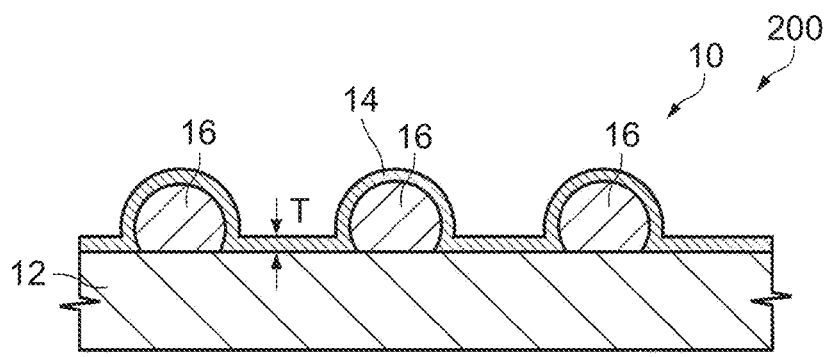
FIG. 16 is a cross-sectional view diagrammatically showing an optical device of a Raman spectroscopic apparatus according to a first variation of the present embodiment.

A Raman spectroscopic apparatus according to a first variation of the present embodiment will be described next with reference to the drawings. FIG. 16 is a cross-sectional view diagrammatically showing the optical device 10 of a Raman spectroscopic apparatus 200 according to the first variation of the present embodiment.

The Raman spectroscopic apparatus 200 according to the first variation of the present embodiment will be described below about points different from those in the Raman spectroscopic apparatus 100 according to the present embodiment, and the same points will not be described. The same holds true for the Raman spectroscopic apparatus according to the second, third, and fourth variations, which will be described below.

In the Raman spectroscopic apparatus 100, the second structural members 16 are disposed so that they are spaced apart from the first structural members 14 by the spacing of 5 nm or less, as shown in FIG. 2. In contrast, in the Raman spectroscopic apparatus 200, a first structural member 14 is disposed so that it coats (e.g., entirely surrounds or encases a free surface of) second structural members 16, as shown in FIG. 16. That is, the first structural member 14 is provided so that it is in contact with the second structural members 16. In the example shown in FIG. 16, the first structural member 14 is also provided on the substrate 12 (upper surface of substrate 12).

In the example shown in FIG. 16, the first structural member 14 completely covers the surfaces of the second structural members 16 not in contact with the substrate 12. However, part of the surfaces of the second structural members 16 may be exposed through the first structural member 14 as long as the first structural member 14 can provide a chemical enhancement effect.

Figure 17:
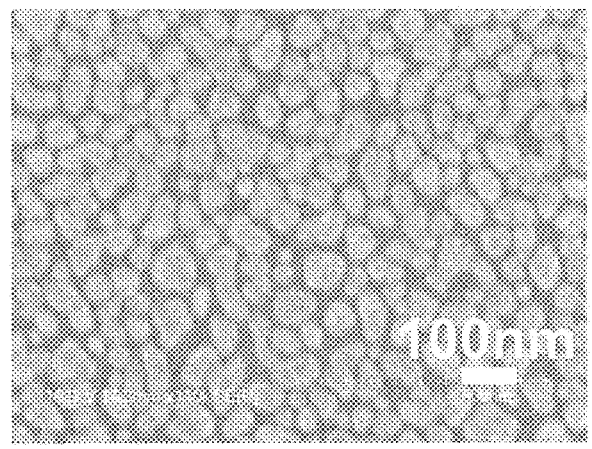
FIG. 17 is a SEM photograph of an island-shaped Ag structure.

A method for manufacturing the optical device 10 of the Raman spectroscopic apparatus 200 will be described. The second structural members 16 are first formed on the substrate 12. The second structural members 16 are formed, for example, by forming an Ag film in a vacuum evaporation process at a film formation speed ranging from 0.1 to 1 angstrom per second. Forming the Ag film under the conditions described above allows formation of an island-shaped Ag structure in a self-assembled manner, as illustrated in the SEM photograph shown in FIG. 17. The first structural member 14 is next formed on the second structural members 16 and the substrate 12. The first structural member 14 is formed, for example, by forming an Al film in a vacuum evaporation process. The optical device 10 can be manufactured by carrying out the steps described above.

Figure 18:
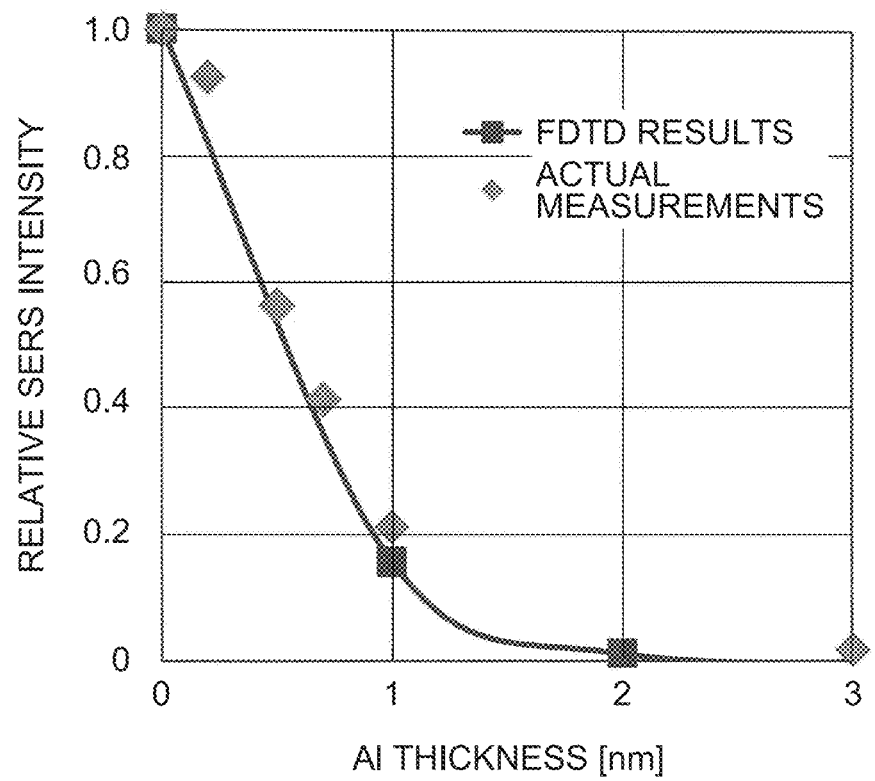
FIG. 18 shows graphs illustrating the relationship between Al thickness and relative SERS intensity.

In the Raman spectroscopic apparatus 200, the first structural member 14 preferably has a thickness (specifically, film thickness of first structural member 14 on substrate 12) T less than or equal to 1 nm, as shown in FIG. 16. The thus sized first structural member 14 allows enhancement of the electric field enhancement effect based on LSPR. FIG. 18 shows graphs illustrating the relationship between the thickness of the first structural member 14 (Al) and a relative SERS intensity (SERS intensity normalized with respect to SERS intensity in a case where Al thickness is zero). FIG. 18 shows calculated plots from an FDTD (finite-difference time-domain) calculation simulation and actual measurements for the optical device formed by using the manufacturing method described above.

The relative SERS intensity decreases as the Al thickness increases and becomes extremely small when the Al thickness becomes greater than 1 nm, as shown in FIG. 18. An estimated reason for this is that when the Al thickness is large, the Ag particles (second structural members 16) are electrically connected to each other, which prevents localization of free electrons under LSPR.

The Raman spectroscopic apparatus 200 differs from the Raman spectroscopic apparatus 100 in that the optical device 10 can be formed in simpler manufacturing steps. Further, in the Raman spectroscopic apparatus 200, setting the thickness of the first structural member 14 at 1 nm or less allows enhancement of the electric field enhancement effect.

5.2. Second Variation

Figure 19:
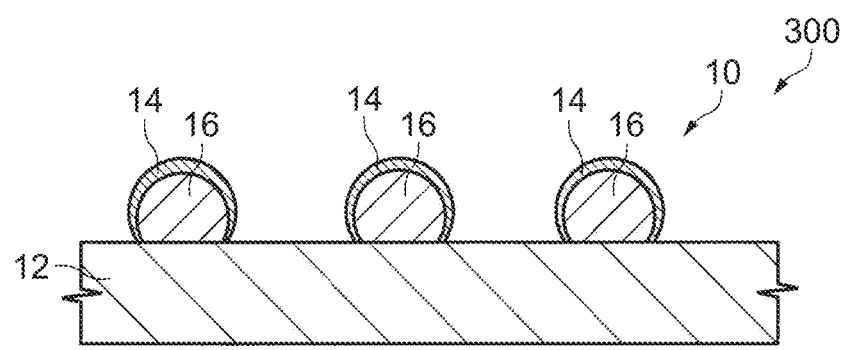
FIG. 19 is a cross-sectional view diagrammatically showing an optical device of a Raman spectroscopic apparatus according to a second variation of the present embodiment.

A Raman spectroscopic apparatus according to a second variation of the present embodiment will be described next with reference to the drawings. FIG. 19 is a cross-sectional view diagrammatically showing the optical device 10 of a Raman spectroscopic apparatus 300 according to the second variation of the present embodiment.

In the Raman spectroscopic apparatus 100, the second structural members 16 are disposed so that they are spaced apart from the first structural members 14 by the spacing of 5 nm or less, as shown in FIG. 2. In contrast, in the Raman spectroscopic apparatus 300, the first structural members 14 are disposed so that they coat (e.g., entirely surround or encases a free surface of) the second structural members 16 and the plurality of first structural members 14 are spaced apart from each other, as shown in FIG. 19. That is, the first structural members 14 are provided so that they are in contact with the second structural members 16. In the example shown in FIG. 19, part of the upper surface of the substrate 12 is exposed. The first structural members 14 may be provided so that they are spaced apart from (not in contact with) the substrate 12.

In the example shown in FIG. 19, the first structural members 14 completely cover the surfaces of the second structural members 16 not in contact with the substrate 12. However, part of the surfaces of the second structural members 16 may be exposed through the first structural members 14 as long as the first structural members 14 can provide a chemical enhancement effect.

Figure 20A:
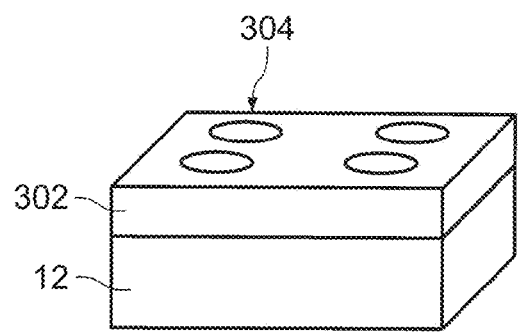
FIG. 20A is a perspective view diagrammatically showing a step of manufacturing the Raman spectroscopic apparatus according to the second variation of the present embodiment.
Figure 20B:
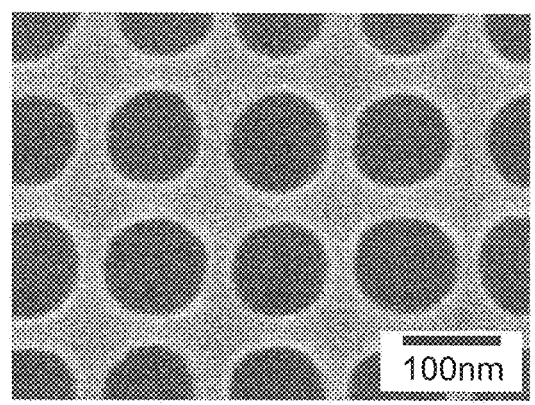
FIG. 20B is a SEM photograph showing the manufacturing step.
Figure 21A:
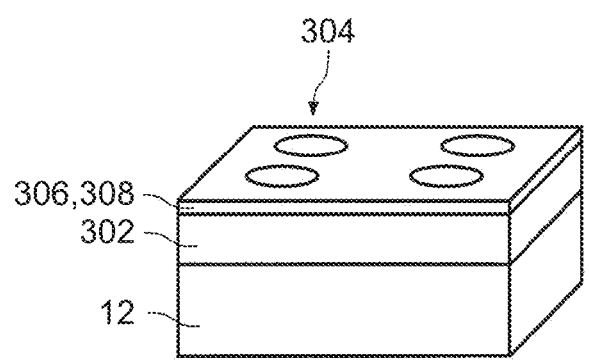
FIG. 21A is a perspective view diagrammatically showing another step of manufacturing the Raman spectroscopic apparatus according to the second variation of the present embodiment.
Figure 21B:
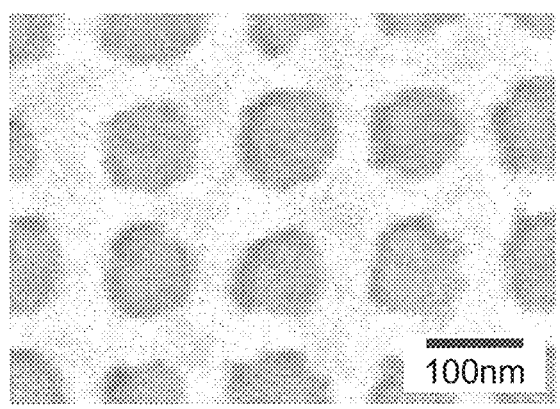
FIG. 21B is a SEM photograph showing the manufacturing step.

A method for manufacturing the optical device 10 of the Raman spectroscopic apparatus 300 will be described with reference to the drawings. FIGS. 20A and 20B to 22A and 20B describe steps of manufacturing the optical device 10 of the Raman spectroscopic apparatus 300 according to the second variation of the present embodiment. FIGS. 20A, 21A, and 22A are perspective views diagrammatically showing the manufacturing steps, and FIGS. 20B, 21B, and 22B are SEM photographs (SEM photographs in plan view) showing the manufacturing steps.

A resist 302 is applied onto the substrate 12 (glass substrate), as shown in FIG. 20A. A two-dimensional array of nano-dots 304, each of which has, for example, a diameter of about 100 nm and which are arranged, for example, at a period of 140 nm, is then formed in the resist 302 in a lithography process using an electron beam drawing method.

Thereafter, for example, an Ag film 306, which will form the second structural members 16, is formed to a thickness of about 30 nm, followed by formation of an Al film 308, which will form the first structural members 14, as shown in FIG. 21A. The Ag film 306 and the Al film 308 are formed, for example, in a vacuum evaporation process.

The resist 302 is lifted off by using a separation liquid, as shown in FIG. 22A. As a result, the Ag film 306 and the Al film 308, which will form the structural members 14 and 16 respectively, can be formed on the substrate 12.

The optical device 10 of the Raman spectroscopic apparatus 300 can be manufactured by carrying out the steps described above.

FIG. 23 shows graphs illustrating the relationship between the thickness of the first structural members 14 (Al) and the relative SERS intensity (SERS intensity normalized with respect to SERS intensity in a case where Al thickness is zero) in the optical device formed by using the manufacturing method described above. The plots shown in FIG. 23 were calculated by using the FDTD calculation simulation. FIG. 23 further shows plots of the FDTD results shown in FIG. 18 for comparison purposes. That is, FIG. 23 shows plots corresponding to the optical device 10 of the Raman spectroscopic apparatus 200 and plots corresponding to the optical device 10 of the Raman spectroscopic apparatus 300.

FIG. 23 shows that the Raman spectroscopic apparatus 300 differs from the Raman spectroscopic apparatus 200 in that increasing the Al thickness does not result in a decrease in the relative SERS intensity. The reason for this is that in the Raman spectroscopic apparatus 300, in which the Al particles (first structural members 14) are not continuously connected to each other, conduction between the Ag particles (second structural members 16) can be prevented.

The Raman spectroscopic apparatus 300 differs from the Raman spectroscopic apparatus 100 in that the optical device 10 can be formed in simpler manufacturing steps and differs from the Raman spectroscopic apparatus 200 in that the electric field enhancement effect can be enhanced irrespective of the thickness of the first structural members 14.

5.3. Third Variation

A Raman spectroscopic apparatus according to a third variation of the present embodiment will be described next.

In the Raman spectroscopic apparatus 100 according to the first variation (see FIG. 2), the first structural members 14 are made of a metal. In contrast, in the Raman spectroscopic apparatus according to the third variation, the first structural members 14 are made of a semiconductor. Preferably, the first structural members 14 are made of silicon.

In the Raman spectroscopic apparatus according to the third variation, the first structural members 14 can be formed by forming a silicon film in a sputtering process and then patterning the silicon film in photolithography and etching processes.

Figure 24:
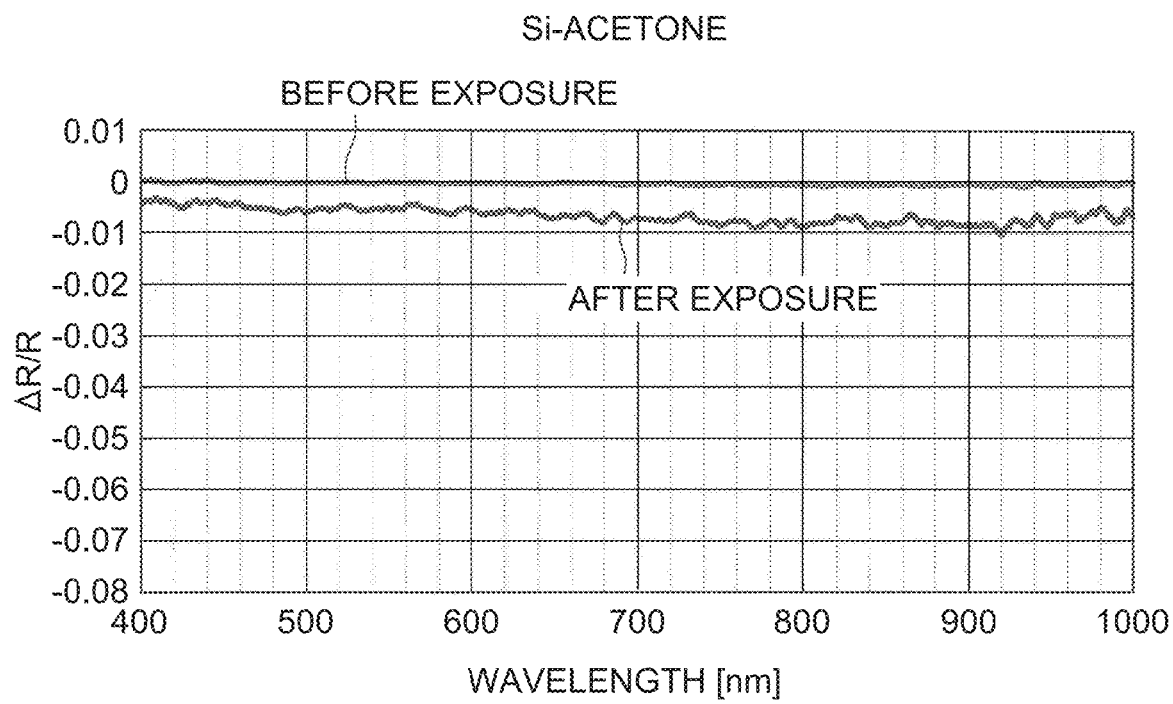
FIG. 24 shows SDRS spectra before and after acetone vapor is exposed to an Si surface.
Figure 25:
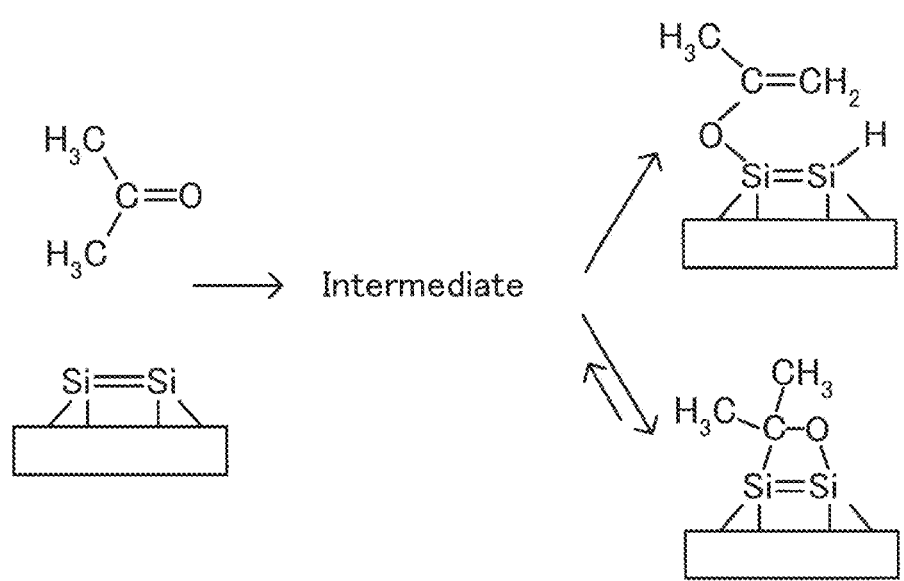
FIG. 25 describes how Si adsorbs acetone.

FIG. 24 shows SDRS spectra before and after acetone vapor is exposed to the Si surface. FIG. 24 shows that after the exposure of acetone, a CT level is present over the visible region. It is believed that Si can chemically adsorb acetone and an Si-acetone complex has a hybrid orbital of the electronic orbital of Si and the molecular orbital of acetone as shown in FIG. 25. It is believed that the result shown in FIG. 24 was obtained based on the assumption described above.

The Raman spectroscopic apparatus according to the third variation is unlikely to corrode due to oxygen, sulfur, and other substances in the air, unlike the Raman spectroscopic apparatus 100. That is, the Raman spectroscopic apparatus according to the third variation is less affected by oxygen, sulfur, and other substances in the air than the Raman spectroscopic apparatus 100 and is hence unlikely to deteriorate.

5.4. Fourth Variation

Figure 26:
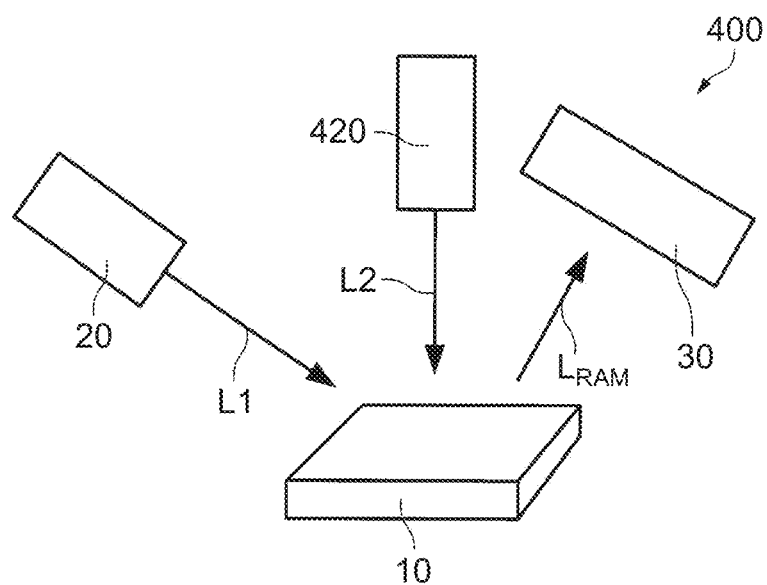
FIG. 26 diagrammatically shows a Raman spectroscopic apparatus according to a fourth variation of the present embodiment.

A Raman spectroscopic apparatus according to a fourth variation of the present embodiment will be described next. FIG. 26 diagrammatically shows a Raman spectroscopic apparatus 400 according to the fourth variation of the present embodiment.

The Raman spectroscopic apparatus 400 includes a light source 420, as shown in FIG. 26. The light source 420 irradiates a target substance with light L2 of a second wavelength having energy corresponding to the difference in energy between the ground state and a minimally excited state of the target substance. That is, the light source 420 irradiates the target substance with the light L2 of the second wavelength having energy corresponding to the difference in energy between the HOMO level and the LUMO level. The second wavelength of the light L2 differs from the first wavelength of the light L1.

Figure 27:
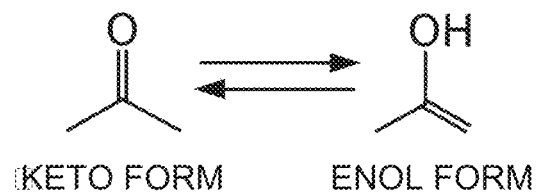
FIG. 27 describes the structure of an acetone molecule.

FIG. 27 describes the structure of an acetone molecule, which is the target substance. Ketones, such as acetone, can have a keto form structure and an enol form structure and typically exists in the keto form, which is stable, and the proportion of the enol form, which is highly reactive, is 0.1% or lower.

Figure 28:
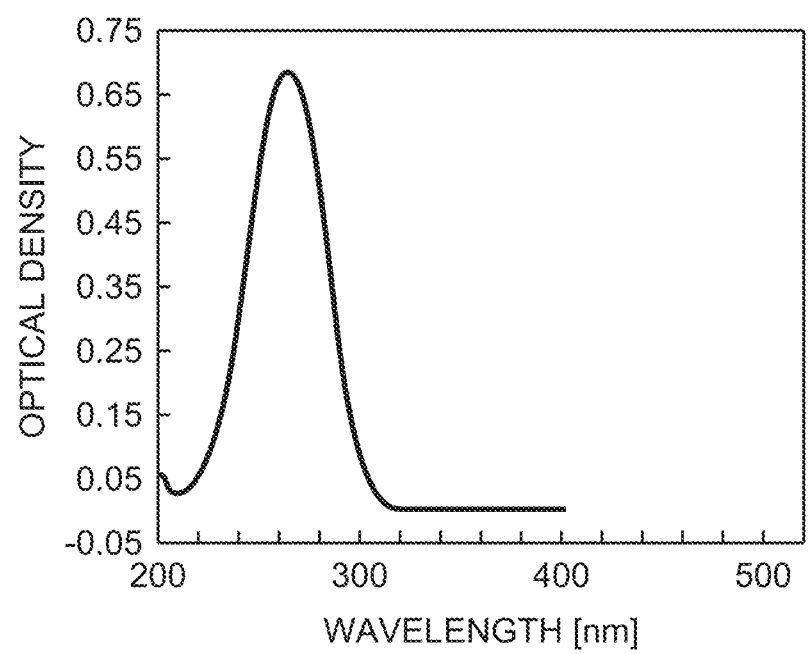
FIG. 28 shows an absorption spectrum of acetone gas alone in a visible-ultraviolet region.

FIG. 28 shows an absorption spectrum of acetone gas alone in a visible-ultraviolet region. An absorption wavelength of acetone is present at a wavelength close to 275 nm, as shown in FIG. 28. The wavelength corresponds to the difference in energy between the HOMO level and the LUMO level of acetone.

In the Raman spectroscopic apparatus 400, the light source 420 can irradiate acetone with the light L2 of the wavelength of 275 nm to change the acetone from the keto form to the enol form shown in FIG. 27. That is, in the Raman spectroscopic apparatus 400, the light L2 of the second wavelength can excite acetone from its ground state to its minimally excited state, whereby the acetone can be more reactive.

Figure 29:
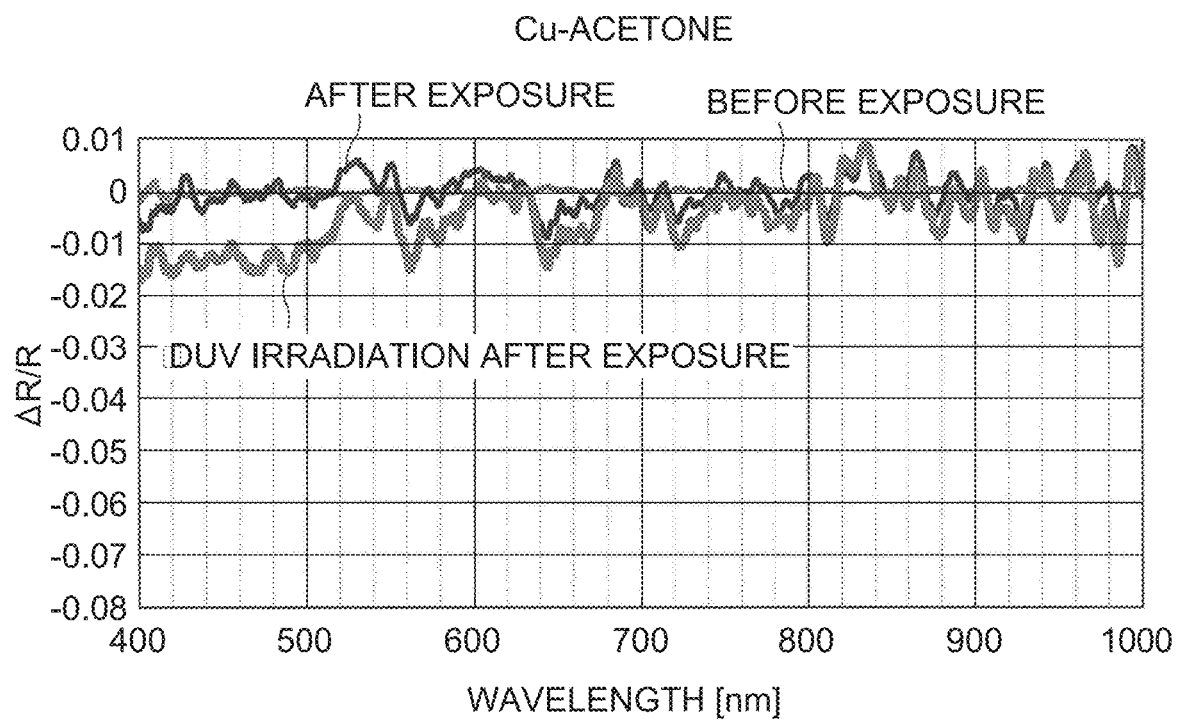
FIG. 29 shows SDRS spectra before and after acetone vapor is exposed to a Cu surface.

FIG. 29 shows SDRS spectra before and after acetone vapor is exposed to a Cu surface. Simply exposing acetone to the Cu surface provides no CT level, as shown in FIG. 29. FIG. 29, however, shows that irradiation of the acetone atmosphere with 275-nm DUV (deep ultraviolet) light provides a CT level in a wavelength region ranging from 400 to 500 nm. The reason for this is that the acetone irradiated with the DUV light is excited to its minimally excited state, which encourages the reaction in which the Cu surface adsorbs the acetone.

In the Raman spectroscopic apparatus 400, in which the target substance is irradiated with the light L2 of the second wavelength having energy corresponding to the difference in energy between the HOMO level and the LUMO level, the reaction in which the first structural members 14 adsorb the target substance is encouraged, whereby the chemical enhancement effect can be enhanced.

6. ELECTRONIC APPARATUS

Figure 30:
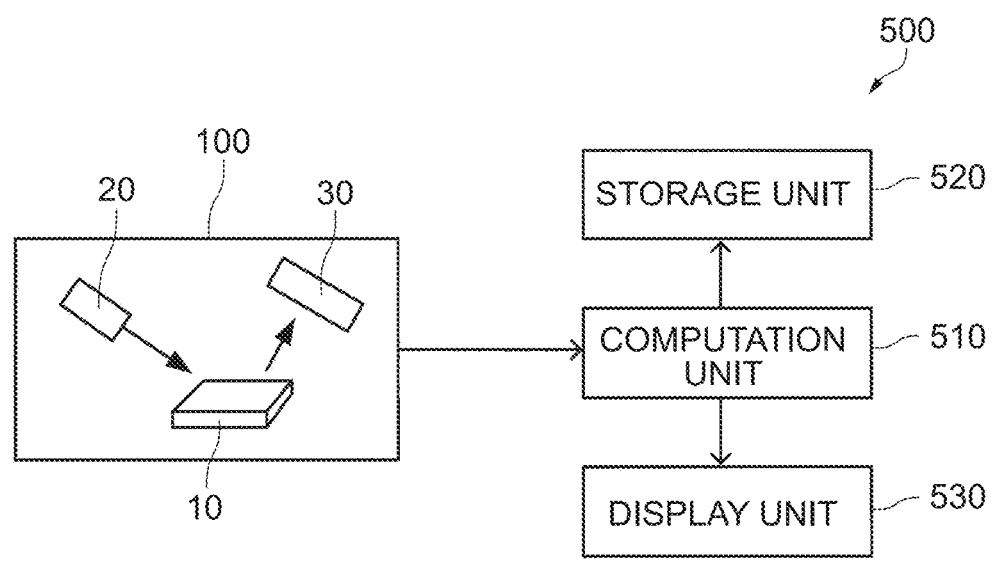
FIG. 30 diagrammatically shows an electronic apparatus according to the present embodiment.

An electronic apparatus 500 according to the present embodiment will be described next with reference to the drawings. FIG. 30 diagrammatically shows the electronic apparatus 500 according to the present embodiment. The electronic apparatus 500 can be equipped with any of the Raman spectroscopic apparatus according to the embodiment of the invention and the variations thereof. A description will be made of the electronic apparatus 500 including the Raman spectroscopic apparatus 100 as the Raman spectroscopic apparatus according to the embodiment of the invention and the variations thereof.

The electronic apparatus 500 includes the Raman spectroscopic apparatus 100, a computation unit 510, which computes healthcare information based on detected information from the optical detector 30, a storage unit 520, which stores the health care information, and a display unit 530, which displays the health care information, as shown in FIG. 30.

The computation unit 510 is, for example, a personal computer or a personal digital assistant (PDA) and receives detected information (such as signal) transmitted from the optical detector 30. The computation unit 510 computes health care information based on the detected information from the optical detector 30. The computed health care information is stored in the storage unit 520.

The storage unit 520 is, for example, a semiconductor memory or a hard disk drive and may be integrated with the computation unit 510. The health care information stored in the storage unit 520 is transmitted to the display unit 530.

The display unit 530 is formed, for example, of a display panel (such as liquid crystal monitor), a printer, a light emitter, a loudspeaker or the like. The display unit 530 displays or issues, based, for example, on the health care information computed by the computation unit 510, information that allows a user to recognize the contents of the health care information.

Examples of the health care information may include information on whether or not there is at least one type of biological substance selected from the group consisting of bacteria, viruses, proteins, nucleic acids, and antigens and antibodies or at least one type of compound selected from inorganic molecules and organic molecules or information on the amount thereof.

The computation unit 510 and the storage unit 520 may be integrated with the controller 130 shown in FIG. 4.

The electronic apparatus 500 includes the Raman spectroscopic apparatus 100, which is capable of detecting Raman scattered light from a target substance in a highly sensitive manner. The electronic apparatus 500 can therefore readily detect a trace quantity of substance and provide highly precise health care information.

The embodiment and the variations described above are examples, and the invention is not limited thereto. For example, the embodiment and the variations can be combined with each other as appropriate.

The scope of the invention encompasses substantially the same configuration as the configuration described in the embodiment (for example, a configuration having the same function, using the same method, and providing the same result or a configuration having the same purpose and providing the same effect). Further, the scope of the invention encompasses a configuration in which an inessential portion of the configuration described in the above embodiment is replaced. Moreover, the scope of the invention encompasses a configuration that provides the same advantageous effect as that provided by the configuration described in the embodiment or a configuration that can achieve the same purpose as that achieved by the configuration described in the embodiment. Further, the scope of the invention encompasses a configuration in which a known technology is added to the configuration described in the embodiment.

The entire disclosure of Japanese Patent Application No. 2013-183944 filed Sep. 5, 2013 is expressly incorporated by reference herein.

What is claimed is:

1. A Raman spectroscopic apparatus comprising:
a light source that emits first wavelength light;
an optical device that adsorbs a substance under analysis and is irradiated with the first wavelength light; and
an optical detector that receives radiated light from the optical device irradiated with the first wavelength light,
wherein the optical device includes:
a first structural member that generates charge transfer resonance in response to irradiation with the first wavelength light, and
a second structural member that is less than or equal to 5 nm from the first structural member and generates surface plasmon resonance in response to irradiation with the first wavelength light,
the first structural member is one of a first metal or a semiconductor, and
the second structural member is a second metal that is different from the one of the first metal or the semiconductor of the first structural member.

2. The Raman spectroscopic apparatus according to claim 1,
wherein the first structural member is coated onto the second structural member.

3. The Raman spectroscopic apparatus according to claim 2,
wherein the first structural member further comprises a plurality of first structural members provided in a plurality of positions, and
the second structural member further comprises a plurality of second structural members provided in a plurality of positions spaced apart from one another.

4. The Raman spectroscopic apparatus according to claim 3,
wherein the plurality of first structural members are spaced apart from each other.

5. The Raman spectroscopic apparatus according to claim 1,
wherein the first structural member has a thickness less than or equal to 1 nm.

6. The Raman spectroscopic apparatus according to claim 1,
wherein the second structural member is one of Ag, Au, or Al.

7. The Raman spectroscopic apparatus according to claim 1,
wherein the substance under analysis is one of acetone or ethanol.

8. The Raman spectroscopic apparatus according to claim 1,
wherein the substance under analysis is acetone,
the first wavelength is greater than or equal to 500 nm but less than or equal to 700 nm, and
a size of the second structural member in a plan view is greater than or equal to 40 nm but less than or equal to 75 nm.

9. The Raman spectroscopic apparatus according to claim 1,
further comprising a second light source that irradiates the substance under analysis with second wavelength light having energy corresponding to a difference in energy between a ground state and a minimally excited state of the substance under analysis.

10. A Raman spectroscopic method comprising:
irradiating an optical device that adsorbed a substance under analysis with first wavelength light, and
receiving radiated light from the optical device irradiated with the first wavelength light,
wherein the optical device includes:
a first structural member that generates charge transfer resonance in response to irradiation with the first wavelength light, and
a second structural member that is less than or equal to 5 nm from the first structural member and generates surface plasmon resonance in response to irradiation with the first wavelength light,
the first structural member is one of a first metal or a semiconductor, and
the second structural member is a second metal that is different from the one of the first metal or the semiconductor of the first structural member.

11. An electronic apparatus comprising:
the Raman spectroscopic apparatus according to claim 1;
a computation unit that computes information based on detected information from the optical detector;
a storage unit that stores the information; and
a display unit that displays the information.

12. The electronic apparatus according to claim 11,
wherein the information includes information on whether there is at least one type of biological substance selected from the group including bacteria, viruses, proteins, nucleic acids, and antigens and antibodies or at least one type of compound selected from inorganic molecules and organic molecules or information on an amount thereof.

13. A Raman spectroscopic apparatus that analyzes a substance under analysis, the apparatus comprising:
   a light source that emits first wavelength light;
   an optical device that adsorbs the substance under analysis and is irradiated with the first wavelength light; and
   an optical detector that receives radiated light from the optical device irradiated with the first wavelength light,
   wherein the optical device includes:
      a substrate,
      a first structural member on the substrate and generating charge transfer resonance in response to irradiation with the first wavelength light, and
      a second structural member on the substrate, the second structural member being less than or equal to 5 nm from the first structural member and generating surface plasmon resonance in response to irradiation with the first wavelength light,
   the first structural member is one of a first metal or a semiconductor, and
   the second structural member is a second metal that is different from the one of the first metal or the semiconductor of the first structural member.

14. The Raman spectroscopic apparatus according to claim 13,
   wherein the first structural member is coated onto the second structural member.

15. The Raman spectroscopic apparatus according to claim 14,
   wherein the first structural member further comprises a plurality of first structural members provided in a plurality of positions, and
   the second structural member further comprises a plurality of second structural members provided in a plurality of positions spaced apart from one another.

16. The Raman spectroscopic apparatus according to claim 15,
   wherein the plurality of first structural members are spaced apart from each other.

17. The Raman spectroscopic apparatus according to claim 13,
   wherein the first structural member has a thickness less than or equal to 1 nm.

18. The Raman spectroscopic apparatus according to claim 13,
   wherein the second structural member is one of Ag, Au, or Al.

19. The Raman spectroscopic apparatus according to claim 13,
   wherein the substance under analysis is one of acetone or ethanol.

20. The Raman spectroscopic apparatus according to claim 13,
   wherein the substance under analysis is acetone,
   the first wavelength is greater than or equal to 500 nm but less than or equal to 700 nm, and
   a size of the second structural member in plan view is greater than or equal to 40 nm but less than or equal to 75 nm.

* * * * *